US011045311B2

(12) United States Patent
Vaturi et al.

(10) Patent No.: US 11,045,311 B2
(45) Date of Patent: Jun. 29, 2021

(54) PROSTHETIC VALVE AND DEPLOYMENT SYSTEM

(71) Applicant: Trisol Medical Ltd., Yokneam (IL)

(72) Inventors: Mordehay Vaturi, Ganei-Tikva (IL); Tal Gollan, Tel-Aviv (IL)

(73) Assignee: Trisol Medical Ltd., Yokneam (IL)

( * ) Notice: Subject to any disclaimer, the term of this patent is extended or adjusted under 35 U.S.C. 154(b) by 0 days.

(21) Appl. No.: 15/535,719

(22) PCT Filed: Dec. 14, 2015

(86) PCT No.: PCT/IL2015/051210
§ 371 (c)(1),
(2) Date: Jun. 14, 2017

(87) PCT Pub. No.: WO2016/098104
PCT Pub. Date: Jun. 23, 2016

(65) Prior Publication Data
US 2018/0085215 A1  Mar. 29, 2018

Related U.S. Application Data

(60) Provisional application No. 62/091,595, filed on Dec. 14, 2014, provisional application No. 62/139,907, filed on Mar. 30, 2015.

(51) Int. Cl.
*A61F 2/24* (2006.01)
*A61F 2/06* (2013.01)
*A61F 2/915* (2013.01)

(52) U.S. Cl.
CPC ............. *A61F 2/2412* (2013.01); *A61F 2/06* (2013.01); *A61F 2/243* (2013.01); *A61F 2/246* (2013.01);
(Continued)

(58) Field of Classification Search
CPC ...... A61F 2220/0008; A61F 2230/0004; A61F 2230/001; A61F 2/06; A61F 2/2412;
(Continued)

(56) References Cited

U.S. PATENT DOCUMENTS 3,671,979 A    6/1972 Moulopoulos
4,218,783 A    8/1980 Reul et al.
(Continued)

FOREIGN PATENT DOCUMENTS

CN    101172059    5/2008
CN    101184456    5/2008
(Continued)

OTHER PUBLICATIONS

Communication Relating to the Results of the Partial International Search dated Nov. 20, 2013 From the International Searching Authority Re. Application No. PCT/IL2012/050469.
(Continued)

*Primary Examiner* — George J Ulsh
*Assistant Examiner* — Andrew P. Restaino

(57) ABSTRACT

A prosthetic heart valve, for example a tricuspid valve, may include a flexible membrane and a frame. The frame may be attached to the periphery of the tricuspid orifice. The diaphragm may be attached to the frame around a part of the perimeter of the orifice. Optionally the frame may be flexible. For example the frame may elastically flex between a substantially circular shape and/of an elliptical and/or crescent shape. Optionally there may not be a stiff cross piece crossing a central region of the orifice and connected on opposing sides of frame. In some embodiments, the diaphragm may take a dome shape during systole.

20 Claims, 20 Drawing Sheets

(52) U.S. Cl.
CPC .......... *A61F 2/2418* (2013.01); *A61F 2/2436* (2013.01); *A61F 2/915* (2013.01); *A61F 2220/0008* (2013.01); *A61F 2230/001* (2013.01); *A61F 2230/0004* (2013.01)

(58) Field of Classification Search
CPC ...... A61F 2/2418; A61F 2/243; A61F 2/2436; A61F 2/246; A61F 2/915; A61F 2/2409; A61F 2/2475
USPC ...................................................... 623/22.11
See application file for complete search history.

(56) References Cited

U.S. PATENT DOCUMENTS

| | | | |
|---|---|---|---|
| 4,553,533 | A | 11/1985 | Leighton |
| 4,561,129 | A | 12/1985 | Arpesella |
| 4,851,000 | A | 7/1989 | Gupta |
| 5,411,552 | A | 5/1995 | Andersen et al. |
| 5,489,297 | A | 2/1996 | Duran |
| 6,200,336 | B1 | 3/2001 | Pavcnik et al. |
| 6,540,782 | B1 | 4/2003 | Snyders |
| 6,989,027 | B2 | 1/2006 | Allen et al. |
| 7,452,371 | B2 | 11/2008 | Pavcnik et al. |
| 7,704,277 | B2 | 4/2010 | Zakay et al. |
| 8,460,370 | B2 | 6/2013 | Zakay et al. |
| 8,932,348 | B2 | 1/2015 | Solem et al. |
| 9,445,893 | B2 | 9/2016 | Vaturi |
| 2003/0199975 | A1 | 10/2003 | Gabbay |
| 2005/0075725 | A1* | 4/2005 | Rowe .................... A61F 2/2418 623/2.14 |
| 2005/0096735 | A1* | 5/2005 | Hojeibane ............. A61F 2/2418 623/1.24 |
| 2005/0228495 | A1 | 10/2005 | Macoviak |
| 2006/0058871 | A1 | 3/2006 | Zakay et al. |
| 2006/0241745 | A1 | 10/2006 | Solem |
| 2007/0005134 | A1 | 1/2007 | McCarthy |
| 2007/0185571 | A1 | 8/2007 | Kapadia et al. |
| 2007/0198097 | A1* | 8/2007 | Zegdi .................... A61F 2/2418 623/23.68 |
| 2007/0270943 | A1 | 11/2007 | Solem et al. |
| 2009/0099653 | A1 | 4/2009 | Suri et al. |
| 2009/0012600 | A1 | 11/2009 | Styrc et al. |
| 2010/0174359 | A1 | 7/2010 | Hefti et al. |
| 2010/0217381 | A1 | 8/2010 | Paul et al. |
| 2010/0280606 | A1 | 11/2010 | Naor |
| 2011/0022157 | A1 | 1/2011 | Essinger et al. |
| 2011/0040374 | A1 | 2/2011 | Goetz et al. |
| 2011/0077733 | A1 | 3/2011 | Solem |
| 2011/0264206 | A1 | 10/2011 | Tabor |
| 2012/0035719 | A1 | 2/2012 | Forster et al. |
| 2012/0101572 | A1 | 4/2012 | Kovalsky et al. |
| 2012/0130468 | A1 | 5/2012 | Khosravi et al. |
| 2012/0323313 | A1 | 12/2012 | Seguin |
| 2013/0226291 | A1 | 8/2013 | Pavcnik et al. |
| 2013/0310928 | A1 | 11/2013 | Morriss et al. |
| 2014/0135908 | A1 | 5/2014 | Glozman et al. |
| 2014/0155990 | A1* | 6/2014 | Nyuli .................... A61F 2/2418 623/2.11 |
| 2014/0172083 | A1 | 6/2014 | Bruchman et al. |
| 2014/0179993 | A1 | 6/2014 | Alexander et al. |
| 2014/0214159 | A1* | 7/2014 | Vidlund .................. A61L 27/34 623/2.14 |
| 2014/0350662 | A1 | 11/2014 | Vaturi |
| 2016/0120646 | A1* | 5/2016 | Dwork .................. A61F 2/2469 623/2.18 |
| 2016/0184098 | A1 | 6/2016 | Vaturi |
| 2016/0235529 | A1* | 8/2016 | Ma ........................ A61F 2/2418 |

FOREIGN PATENT DOCUMENTS

| | | |
|---|---|---|
| CN | 101361683 | 2/2009 |
| CN | 202105047 | 1/2012 |
| CN | 103153232 | 6/2013 |
| FR | 2883721 | 10/2006 |
| JP | 2013-545515 | 12/2013 |
| WO | WO 2004/030568 | 4/2004 |
| WO | WO 2004/089250 | 10/2004 |
| WO | WO 2005/027797 | 3/2005 |
| WO | WO 2010/108079 | 9/2010 |
| WO | WO 2013/022798 | 2/2013 |
| WO | WO 2013/076724 | 5/2013 |
| WO | WO 2014/021905 | 2/2014 |
| WO | WO 2014/022124 | 2/2014 |
| WO | WO 2016/098104 | 6/2016 |

OTHER PUBLICATIONS

International Preliminary Report on Patentability dated Jun. 5, 2014 From the International Bureau of WIPO Re. Application No. PCT/IL2012/050469.

International Preliminary Report on Patentability dated Jun. 29, 2017 From the International Bureau of WIPO Re. Application No. PCT/IL2015/051210. (6 Pages).

International Search Report and the Written Opinion dated Feb. 3, 2014 From the International Searching Authority Re. Application No. PCT/IL2012/050469.

International Search Report and the Written Opinion dated Jul. 26, 2016 From the International Searching Authority Re. Application No. PCT/IL2015/051210.

Invitation to Pay Additional Fees dated May 5, 2016 From the International Searching Authority Re. Application No. PCT/IL2015/51210.

Official Action dated Jun. 19, 2015 From the U.S. Patent and Trademark Office Re. U.S. Appl. No. 14/359,646.

Official Action dated Jun. 37, 2017 From the U.S. Patent and Trademark Office Re. U.S. Appl. No. 15/066,051. (17 pages).

Anwar et al. "Assessment of Tricuspid Valve Annulus Size, Shape and Function Using Real-Time Three-Dimensional Echocardiography", Interactive CardioVascular and Thoracic Surgery, 5: 683-687, 2006.

Colombo et al. "Tricuspid Regurgitation Secondary to Mitral Valve Disease: Tricuspid Annulus Function as Guide to Tricuspid Valve Repair", Cardiovascular Surgery, 9(4): 369-377, 2001.

Dini et al. "Right Ventricular Dysfunction Is A Major Predictor of Outcome in Patients With Moderate to Severe Mitral Regurgitaiton and Left Ventricular Dysfunction", American Heart Journal, 154: 172-179, 2007.

Dreyfus et al. "Secondary Tricuspid Regurgitation or Dilatation: Which Should Be the Criteria for Surgical Repair?", The Annals of Thoracic Surgery, 79(1): 127-132, Jan. 2005.

Dreyfus et al. "Tricuspid Leaflet Augmentation to Address Severe Tethering in Functional Tricuspid Regurgitation", European Journal of Cardio-Thoracic Surgery, 34(4): 908-910, Oct. 2008.

Engstroem et al. "Right Ventricular Dysfunction Is An Independent Predictor for Mortality in ST-Elevation Myocardial Infarction Patients Presenting With Cardiogenic Shock on Admission", European Journal of Heart Failure, 12: 276-282, 2010.

Fukuda et al. "Tricuspid Valve Tethering Predicts Residual Tricuspid Regurgitation After Tricuspid Annuloplasty", Circulation, 111: 975-979, Mar. 1, 2005.

Ghanta et al. "Suture Bicuspidization of the TTricuspid Valve Versus Ring Annuloplasty for Repair of Functional Tricuspid Regurgitation: Midterm Results of 237 Consecutive Patients", The Journal of Thoracic and Cardiovascular Surgery, 133(1): 117-126, Jan. 2007.

Guenther et al. "Tricuspid Valve Surgery: A Thirty-Year Assessment of Early and Late Outcome", European Journal of Cardio-Thoracic Surgery, 34: 402-409, 2008.

Gurvitch et al. "Transcatheter Valve-in-Valve Implantation for Failed Surgical Bioprosthetic Valves", Journal of the American College of Cardiology, 58(21): 2196-2209, 2011.

Kim et al. "Assessment of Haemodynamic Effects of Surgical Correction for Severe Functional Tricuspid Regurgitation: Cardiac Magnetic Resonance Imaging Study", European Heart Journal, 31: 1520-1528, 2010.

Lancellotti et al. "European Association of Echocardiology Recommendations for the Assessment of Valvular Regurgitation.

(56) References Cited

OTHER PUBLICATIONS

Part 2: Mitral and Tricuspid Regurgitaiton (Native Valve Disease)", European Journal of Echocardiography, 11: 307-332, 2010.
McCarthy et al. "Tricuspid Valve Repair: Durability and Risk Factors for Failure", The Journal of Thoracic and Cardiovascular Surgery, 127(3): 674-685, Mar. 2004.
Nath et al. "Impact of Tricuspid Regurgitation on Long-Term Survival", Journal of the American College of Cardiology, JACC, 43(3): 405-409, 2004.
Navia et al. "Surgical Management of Secondary Tricuspid Valve Regurgitation: Annulus, Commissure, or Leaflet Procedure?", the Journal of Thoracic and Cardiovascular Surgery, 139(6): 1473-1482e5, Jun. 2010.
Porter et al. "Tricuspid Regurgitation Late After Mitral Valve Replacement: Clinical and Echocardiographic Evaluation", The Journal of Heart Valve Disease, 8(1): 57-62, Jan. 1999. Abstract.
Roberts et al. "Percutaneous Tricuspid Valve Replacement in Congenital and Acquired Heart Disease", Journal of the American College of Cardiology, 58(2): 117-122, 2011.
Sengupta et al. "RV Form and Function. A Piston Pump, Vortex Impeller, or Hydraulic Ram?", Journal of the American College of Cardiology, JACC: Cardiovascular Imaging, 6(5): 636-639, May 2013.
Taramasso et al. "The Growing Clinical Importance of Secondary Tricuspid Regurgitation", Journal of the American College of Cardiology, JACC, 59(8): 703-710, 2012.
Tei et al. "The Tricuspid Valve Annulus: Study of Size and Motion in Normal Subjects and in Patients With Tricuspid Regurgitation", Circulation, 66(3): 665-671, Sep. 1982.
Notification of Office Action dated Mar. 20, 2018 From the State Intellectual Property Office of the People's Republic of China Re. Application No. 201580068004.6. (4 Pages).
Translation Dated Apr. 12, 2018 of Notification of Office Action dated Mar. 20, 2018 From the State Intellectual Property Office of the People's Republic of China Re. Application No. 201580068004.6. ( 5 Pages).
Supplementary European Search Report and the European Search Opinion dated Jul. 6, 2018 From the European Patent Office Re. Application No. 15869467.9. (7 Pages).
Notification of Office Action and Search Report dated Nov. 16, 2018 From the State Intellectual Property Office of the People's Republic of China Re. Application No. 201580068004.6. (7 Pages).
Translation Dated Dec. 13, 2018 of Notification of Office Action and Search Report dated Nov. 16, 2018 From the State Intellectual Property Office of the People's Republic of China Re. Application No. 201580068004.6. (8 Pages).
Notification of Office Action and Search Report dated Jul. 15, 2019 From the State Intellectual Property Office of the People's Republic of China Re. Application No. 201580068004.6. (7 Pages).
Translation Dated Aug. 5, 2019 of Notification of Office Action dated Jul. 15, 2019 From the State Intellectual Property Office of the People's Republic of China Re. Application No. 201580068004.6. (7 Pages).
Notice of Reasons for Rejection dated Nov. 12, 2019 From the Japan Patent Office Re. Application No. 2017-530193. (5 Pages).
Translation Dated Nov. 27, 2019 of Notice of Reasons for Rejection dated Nov. 12, 2019 From the Japan Patent Office Re. Application No. 2017-530193. (8 Pages).
Search Report and Explanations dated Mar. 13, 2020 From the Servico Publico Federal, Ministerio da Economia, Instituto Nacional da Propriedade Industrial do Brasil Re. Application No. BR112017012669-9 and Its Summary in English. (5 Pages).
Notice of Reasons for Rejection dated Oct. 27, 2020 From the Japan Patent Office Re. Application No. 2017-530193. (6 Pages).
Translation Dated Nov. 13, 2020 of Notice of Reasons for Rejection dated Oct. 27, 2020 From the Japan Patent Office Re. Application No. 2017-530193. (10 Pages).
Examination Report Under Section 12 & 13 of the Patents Act, 1970 and the Patents Rules, 2003 dated Jul. 22, 2020 From the Government of India, Intellectual Property India, Patents, Designs, Trade Marks, Geographical Indications, The Patent Office Re. Application No. 201727023688. (9 Pages).
Office Action dated Jul. 14, 2020 From the Israel Patent Office Re. Application No. 252859. (4 Pages).
Translation Dated Jul. 29, 2020 of Office Action dated Jul. 14, 2020 From the Israel Patent Office Re. Application No. 252859. (3 Pages).

* cited by examiner

PROSTHETIC VALVE AND DEPLOYMENT SYSTEM

RELATED APPLICATIONS

This application is a National Phase of PCT Patent Application No. PCT/IL2015/051210 having International filing date of Dec. 14, 2015, which claims the benefit of priority under 35 USC § 119(e) of U.S. Provisional Patent Application Nos. 62/091,595 filed on Dec. 14, 2014 and 62/139,907 filed on 30 Mar. 2015. The contents of the above applications are all incorporated by reference as if fully set forth herein in their entirety.

FIELD AND BACKGROUND

Embodiments disclosed herein generally relate to a prosthetic valve and, more particularly, but not exclusively, to a prosthetic replacement for a tricuspid valve and catheter delivery system.

US Patent Publication No. 20050228495 to Macoviak discloses a valve prosthesis that, "is sized and configured to rest within a blood path subject to antegrade and retrograde blood flow. A trestle element on the prosthesis extends across the blood path. A leaflet assembly is suspended from the trestle element and extends into the blood path in alignment with blood flow. At least one mobile leaflet member on the leaflet assembly is sized and configured to assume orientations that change according to blood flow direction. The mobile leaflet member has a first orientation that permits antegrade blood flow and a second orientation that resists retrograde blood flow. The valve prosthesis, when implanted in a heart chamber or great vessel, serves to supplement and/or repair and/or replace native one-way heart valve function."

U.S. Pat. No. 4,561,129 to Arpesella "relates to a 'biological' valve suitable for surgical treatment of cardiopathies, composed of a supporting ring having a diametrically-disposed element which functions as a support for the hinge of the two flaps which alternately allow and prevent flow through the device. It is designed in such a way that the angle formed by these flaps in the resting position conditions both the height of the prosthesis as well as the mechanical behavior of the aforementioned flaps."

US Patent Publication No. 20110264206 to Tabor relates to "prosthetic valves having sealing members on the external surface thereof. The prosthetic heart valves of the present invention are preferably delivered by catheter directly through the apex of the heart or by other close range transcatheter delivery methods . . . "

US Patent Publication No. 20110040374 to Goetz et al. relates to "A replacement valve for implantation centrally within the orifice of a malfunctioning native heart valve. The valve is designed for minimally invasive entry through an intercostal opening in the chest of a patient and an opening in the apex of the human heart. The replacement valve includes either a separate anchor or a combined anchor that folds around the malfunctioning native valve leaflets, sandwiching them in a manner so as to securely anchor the replacement valve in a precise, desired location."

International Patent Publication No. WO 2013076724 to Vaturi relates to "A method and a device for implantation in or near an annulus of a tricuspid valve comprising at least one blood flow control element adapted to capture a volume of blood therein."

SUMMARY

According to an aspect of a first embodiment, there is provided a prosthetic valve, comprising: a frame sized and shaped to fit in an orifice, the frame having a minimum external perimeter and a minimum cross section; a flexible diaphragm including an edge at least as large as a the minimum external perimeter of the frame and a side of the diaphragm having a surface area greater than a the minimum cross section of the frame; the flexible diaphragm is connected to the frame along a length ranging between 1% and 25% of a length of the edge such that a portion of the diaphragm is held partially expanded along the length.

According to a second embodiment and optionally according to the first embodiment, the length of connection of the diaphragm to the frame ranges between 1% and 25% of the minimum external perimeter.

According to a third embodiment and optionally according to any of the first to the second embodiments, the length of connection of the diaphragm to the frame is along a peripheral portion of the orifice.

According to a fourth embodiment and optionally according to any of the first to the third embodiments, the length of connection of the diaphragm to the frame ranges includes between 1% and 25% of a perimeter of the orifice.

According to a fifth embodiment and optionally according to any of the first to the fourth embodiments, the flexible diaphragm forms a dome.

According to a sixth embodiment and optionally according to any of the first to the fifth embodiments, the frame has a downstream border and wherein the edge of the flexible diaphragm is at least as large as a perimeter of the frame at the downstream border.

According to a seventh embodiment and optionally according to any of the first to the sixth embodiments, the frame has a downstream border and wherein the side of the diaphragm has a surface area greater than a cross section of the frame at the downstream border.

According to an eighth embodiment and optionally according to any of the first to the seventh embodiments, the frame surrounds a simply connected space and the diaphragm divides the simply connected space into at least two disconnected channels.

According to a ninth embodiment and optionally according to any of the first to the eighth embodiments, the frame has an axial length of between 10 to 20 mm.

According to a tenth embodiment and optionally according to any of the first to the ninth embodiments, the frame has an axial length of between 20 to 30% of the perimeter the orifice.

According to an eleventh embodiment and optionally according to any of the first to the tenth embodiments, the length of connection of the diaphragm to the frame ranges includes between 2% and 7% of the perimeter of the orifice.

According to a twelfth embodiment and optionally according to any of the first to the eleventh embodiments, the diaphragm is connected to the frame only along the length of connection of the diaphragm to the frame.

According to a thirteenth embodiment and optionally according to any of the first to the twelfth embodiments, the orifice is a tricuspid annulus.

According to a fourteenth embodiment and optionally according to any of the first to the thirteenth embodiments, the diaphragm has a collapsed position allowing flow from an upstream direction to a downstream direction on at least two sides of the diaphragm and an expanded position inhibiting the flow.

According to a fifteenth embodiment and optionally according to any of the first to the fourteenth embodiments, the diaphragm includes a free region including a downstream apex.

According to a sixteenth embodiment and optionally according to the fifteenth embodiment in the expanded position, the apex is upstream of the frame.

According to a seventeenth embodiment and optionally according to any of the first to the sixteenth embodiments, the diaphragm has a smooth dome shape.

According to an eighteenth embodiment and optionally according to any of the fifth to the seventeenth embodiments, the dome in the expanded position has a convex outer surface.

According to a nineteenth embodiment and optionally according to any of the fifth to the eighteenth embodiments, the dome in the expanded position has a smooth outer surface.

According to a twentieth embodiment and optionally according to any of the first to the nineteenth embodiments, the frame flexes such that a ratio of a length of an axis of the frame during diastole with respect to a length of the axis during systole is at least 1.3 to 1.

According to a twenty first embodiment and optionally according to any of the first to the twentieth embodiments, the prosthetic valve wherein the frame does not include a stiff cross piece connecting two sides of the frame.

According to a twenty second embodiment and optionally according to any of the first to the twenty first embodiments, wherein there is no stiff element connected on two sides to the frame and crossing a free area includes a projection of at least 40 of the a cross section of the orifice including a center of the orifice.

According to a twenty third embodiment and optionally according to any of the first to the twenty second embodiments, a concave side of the dome faces a downstream direction.

According to a twenty fourth embodiment and optionally according to any of the first to the twenty third embodiments, the diaphragm has a collapsed position allowing flow from an upstream direction to a downstream direction between the diaphragm and the perimeter of the orifice and an expanded position inhibiting the flow.

According to an aspect of a twenty fifth embodiment, there is provided a delivery system for a prosthetic heart valve comprising: an extender including a first portion (1391 in FIGS. 13 and 16) with a proximal end located proximal to the prosthetic heart valve, the first portion extending through a flow channel (666a in FIG. 13) of the prosthetic heart valve and a second portion located distal to the prosthetic heart valve; a delivery knurl mounted on the second portion (1393 in FIGS. 13 and 16) of the extender; and a guide wire channel (dashed lines 1395 in FIG. 16) extending through the delivery knurl.

According to a twenty sixth embodiment and optionally according to the twenty fifth embodiment, the delivery system further comprises; a guide wire extending from a proximal side of the prosthetic valve through a second flow channel (666b in FIG. 13) of the prosthetic valve and further extending through the guide wire channel.

According to a twenty seventh embodiment and optionally according to any of the twenty fifth to the twenty sixth embodiments, the delivery system further comprises; a guide wire extending from a proximal side of the prosthetic valve through the flow channel of the prosthetic valve and further extending through the guide wire channel.

According to a twenty eight embodiment and optionally according to any of the twenty fifth to the twenty seventh embodiments, the flow channel is a peripheral flow channel.

According to an aspect of a twenty ninth embodiment, there is provided a method of controlling flow through an orifice comprising: suspending a diaphragm on a periphery of the orifice; collapsing the diaphragm by means of a pressure gradient in a first direction through the orifice the pressure gradient in the first direction driving flow passing between the periphery and the diaphragm on at least on two sides of the diaphragm; filling the diaphragm with regurgitated fluid driven by a second pressure gradient in a second direction opposite the first direction, and pressing the diaphragm against a periphery of the orifice by fluid pressure from the second gradient.

According to a thirtieth embodiment and optionally according to the twenty ninth embodiment, the method of controlling further comprises: retaining an apex of the diaphragm upstream of the frame during the repeated flexing.

According to a thirty first embodiment and optionally according to any of the twenty ninth to the thirtieth embodiments, the method of controlling further comprises: resuming the pressure gradient in the first direction after the filling and returning at least 80% of the regurgitated fluid to a back through the orifice during the resuming.

According to a thirty second embodiment and optionally according to any of the twenty ninth to the thirty first embodiments, the suspending includes dividing an internal a simply connected cross section into at least two disconnected channels.

According to a thirty third embodiment and optionally according to any of the twenty ninth to the thirty second embodiments, the method of controlling further includes: fitting a frame into orifice and wherein the suspending is from a frame fit into the orifice.

According to a thirty fourth embodiment and optionally according to any of the twenty ninth to the thirty third embodiments, the method of controlling further comprises: repeatedly elastically flexing the frame between two geometries having respective aspect ratios of greater than 1.3 to 1.

According to a thirty fifth embodiment and optionally according to any of the twenty ninth to the thirty fourth embodiments, the method of controlling further comprises: delivering the diaphragm to the orifice in a catheter.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS

Overview

Figure 1:
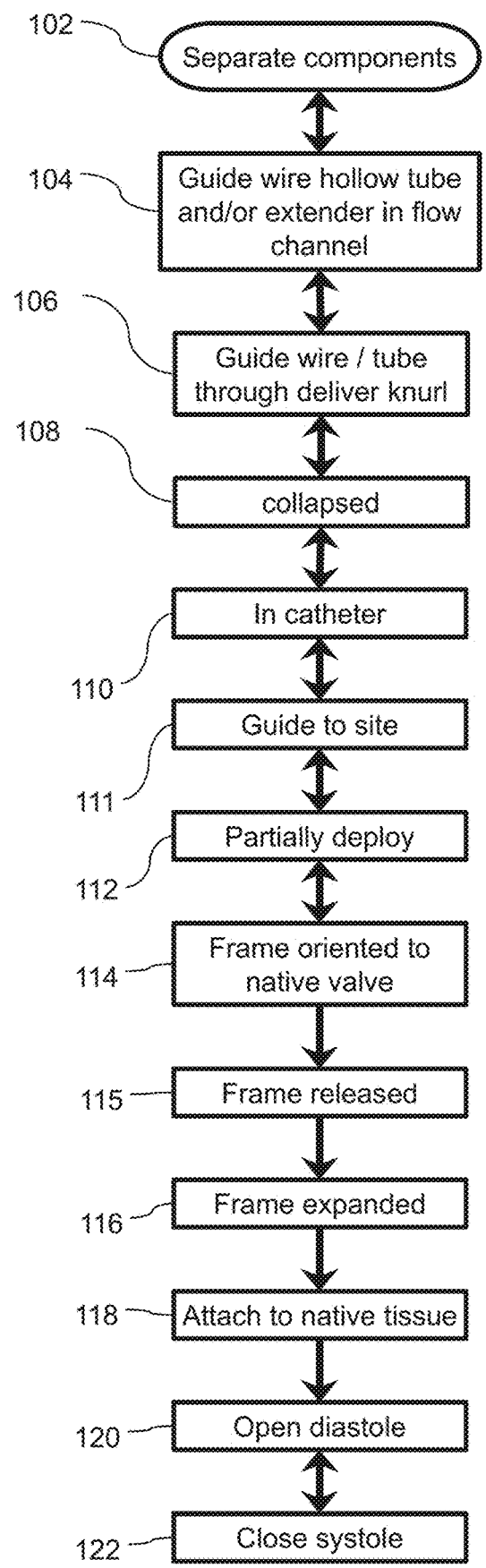
FIG. 1 is a state diagram of a prosthetic valve and/or a delivery system in accordance with some embodiments.

Aspects of disclosed embodiments relates to a prosthetic valve and, more particularly, but not exclusively, to a prosthetic replacement for a tricuspid valve and catheter delivery system for the prosthetic valve replacement.

An aspect of some embodiments relates to a peripheral flow prosthetic valve. Optionally the valve includes a diaphragm supported by a connection to the frame along a length of the frame. When the valve is open, the diaphragm is optionally collapsed. For example the two sides of the diaphragm may collapse toward the center. Optionally, the portion of the diaphragm connected to the frame is held expanded and/or open along the length of said connection to the frame. For example, flow from an upstream region to a downstream region causes said diaphragm to collapse and/or opens said valve. For example, flow from a downstream region to an upstream region is trapped in the expanded and/or open portion of the diaphragm and/or expands the diaphragm and/or closes the valve.

Optionally the apex of the diaphragm faces in the upstream direction. Optionally the apex of the diaphragm may remain upright when the dome collapses. When the valve is open, flow optionally passes between the diaphragm and the periphery of the orifice. For example, flow may pass the diaphragm on at least two opposing sides thereof. When the valve is closed the free edge of the diaphragm may optionally expand against the periphery of the orifice and/or the frame and/or a skirt connected to the frame. Expanding the diaphragm against the periphery of the orifice optionally closes the valve and/or or impedes flow through the orifice to flow. For example fluid pressure may push the flexible diaphragm against the inner walls of orifice and/or the frame.

In some embodiments, the diaphragm may be dome shaped when the diaphragm is spread and/or when the valve is closed to flow. For example the concave side of the diaphragm may be facing downstream. Optionally the apex of the dome extends upstream beyond the frame.

In some embodiments, the frame may be flexible. For example, a tricuspid orifice and/or the frame may take an elliptical and/or half moon shape during systole and/or a circular shape during diastole. The closing of the valve may be substantially unaffected by the flexing of the frame. Optionally, the valve allows controlled regurgitation. For example the dome shaped membrane optionally captures a predetermined quantity of blood during systole. Some or/all of the captured blood is optionally returned during diastole.

In some embodiments, the diaphragm is made of a single piece of material. Alternatively or additionally the diaphragm may be made of multiple pieces. Optionally the diaphragm may include one or more leaflets. Optionally, the diaphragm material may be a flexible biocompatible polymer, pericardium and/or include bovine and/or porcine pericardium.

In some embodiments, the diaphragm may fill with fluid like parachute, a sail and/or a balloon. For example, during systole, the diaphragm may take a dome and/or parabolic shape. For example the shape of the dome may change with deformations of the frame, for example between systole and diastole.

Optionally the supports of the diaphragm on the periphery may hold the diaphragm in a ready position during flow through the valve. For example, the supports may hold the diaphragm partially extended when the valve is open. For example, for a tricuspid prosthesis, attachment to the periphery of a tricuspid orifice may hold a portion of parachute type diaphragm expanded during diastole. The partially expanded diaphragm optionally catches fluid during systole, further expanding the diaphragm and/or closing the valve and/or closing off the orifice and/or impeding flow through the orifice.

In some embodiments, an apex of the diaphragm may extend past the edge of a frame of the valve. For example the apex of the diaphragm may extend in an upstream direction from the frame ranging between 0 to 12 mm and/or between 12 to 22 mm and/or between 22 to 30 mm. In some embodiments, the unstressed length of the edge of the diaphragm may be larger than the perimeter of the orifice. Additionally or alternatively, the edge of the diaphragm may be smaller than the perimeter of the orifice. The edge of the diaphragm optionally extends against the perimeter of the orifice under fluid pressure and/or closes the valve. For example the length of the edge of the diaphragm may range between 0.5 to 1 times the perimeter of the orifice and/or between 1 to 1.2 times the perimeter of the orifice and/or between 1 to 1.2 times the perimeter of the orifice and/or between 1.2 to 1.6 times the perimeter of the orifice and/or between 1.6 to 3 times the perimeter of the orifice. In some embodiments, the surface area of one side of the diaphragm may be greater than the area of a circle having the same perimeter length as the diaphragm. For example the surface area of the diaphragm may range between 1.5 to 3 times the area of a circle having the same perimeter length as the diaphragm and/or between 3 to 5 times the area of a circle having the same perimeter length as the diaphragm and/or between 5 to 10 times the area of a circle having the same perimeter length as the diaphragm. In some embodiments, the surface area of the diaphragm may be greater than the cross sectional area of the orifice. For example the surface area of the diaphragm may range between 1.5 to 3 times the cross sectional area of the orifice and/or between 3 to 5 times the cross sectional area of the orifice and/or between 5 to 10 times the cross sectional area of the orifice and/or more than 10 times the cross sectional area of the orifice.

In some embodiments, the frame may include one or more support elements extending into the orifice. For example the support elements may extend between 0 to 2 mm and/or between 2 to 5 mm and/or between 5 to 15 mm upstream of the peripheral portion of the frame. Alternatively or additionally, a support element may be surrounded by and/or within the peripheral portion of the frame. In some embodiments, the support elements do not reach the center of the orifice and/or are connected to only one side of the orifice. For example a support element may have cantilever geometry, for example only one side of the support element may be attached to the periphery of the frame and/or periphery of the orifice. Optionally the support elements may extend 0 to 3 mm and/or 3 to 6 mm and/or 6 to 10 mm from the periphery towards the center of the orifice. Alternatively or additionally a support element may cross the orifice and/or may be attached at both ends and/or at multiple points to the periphery of the frame and/or orifice. Optionally a support element may be located on the upstream side and/or the downstream side of the diaphragm. Optionally the diaphragm is attached (for example by sutures) to one or more support elements.

An aspect of some embodiments relates to a prosthetic valve with controlled regurgitation. Optionally the valve includes a parachute diaphragm and/or a balloon diaphragm and/or a sail diaphragm that fills with blood when flow is blocked. For example, the valve may be used as a tricuspid prosthesis. The diaphragm may fill with between 0 to 10 ml and/or between 10 to 20 ml and/or between 20 to 30 ml and/or 30 to 40 ml of fluid as it seals off an orifice impeding and/or inhibiting and/or preventing further regurgitation. For example, for a tricuspid prosthesis during systole, the parachute may fill with a volume between 0 to 10% and/or 10 to 20% and/or 20 to 30% and/or 30 to 40% of the volume of the ventricle to which the valve is attached. Part and/or all of the blood that filled the parachute is optionally returned to the ventricle during diastole.

One issue that may occur with defective native valves is regurgitation. While there is excess regurgitation, the cardiac muscle may sometimes contract with a greater increased force and/or volume. In some cases increased stroke may compensate for the regurgitation and/or sustain cardiac output. This process gradually has been hypothesized to lead in some cases to cardiac muscle remodeling and/or eventually to systolic dysfunction due to reduced contractility. In some cases remodeling may be followed by even greater regurgitation, for example due to dilatation of the ventricle and/or increased tethering of the valve and/or pulmonary edema and/or systemic venous congestion.

In some cases, an abrupt cease of regurgitation may lead and/or an acute increase in afterload on the ventricle. In some cases the consequence may be deleterious to the ventricle. Optionally some embodiments of a prosthetic valve may reduce regurgitation and/or allow mild regurgitation (for example hemodynamically insignificant to the heart). Optionally the controlled and/or mild regurgitation may ease the afterload on the ventricle. Optionally, during systole the volume of the diaphragm may effectively be added to the volume of the ventricle. For example, temporarily increasing the volume of the ventricle may reduce the load on the ease the afterload on the ventricle.

In some embodiments controlled regurgitation may be supplied by one or more holes in the diaphragm. A hole may be located at the center of the diaphragm and/or non-centered. The total area of the holes may range, for example between 0.2 $mm^2$ and 0.8 $mm^2$ and/or between 0.8 $mm^2$ and 2 $mm^2$ and/or between 2 $mm^2$ and 15 $mm^2$ and or between 15 $mm^2$ and 25 $mm^2$.

An aspect of some embodiments relates to a prosthetic valve with a flexible frame. Optionally the frame may change shape with the annulus of the natural orifice. For example in a tricuspid annulus, the frame may take an oval shape during systole and/or a more circular shape during diastole. Optionally the valve includes a parachute like diaphragm that may be pushed against the wall of the orifices (for example the inner walls of the frame and/or a skirt). Pushing the diaphragm against the wall of the orifice optionally closes the orifice to back flow and/or regurgitation. For example, fluid pressure may push the diaphragm evenly against the inner walls of the frame and/or orifice. For example, fluid pressure may be applied evenly and/or close the valve evenly substantially independent of the geometry of the orifice. Optionally, the frame may not include a stiff member limiting the length of an axis of the frame's cross section (for example a transverse axis). For example, the frame may not include any stiff crosspiece. Optionally the frame may not be limited by any stiff member connected on opposing sides of a central region of the frame. For example, the frame may define a simply connected interior region and/or a single flow channel. The diaphragm is optionally suspended across the frame dividing said simply connected flow channel into at least two channels. For example, without the diaphragm, a cross section of the frame and/or a two dimensional projection of the cross section of the frame may include a single simply connected interior region. For example, with the diaphragm, a cross section of the frame and diaphragm and/or a two dimensional projection of the cross section of the frame and diaphragm may include at least two disconnected interior regions.

In some embodiments, the diaphragm may be connected to and/or contact the frame at nearly tangential angle (for example ranging between 0 to 5 degrees of tangential and/or between 5 and 15 degrees and/or between 15 and 30 degrees). This may lead to reduced radial forces on the frame and/or allow use of a more compliant and/or flexible frame. This may sometimes may fluid pressure more effective in closing the valve. For example the radial forces on the frame and/or on the closing interface of the valve may be substantially pressure forces. Optionally, the net force and/or the pressure force on the diaphragm along a portion of inner wall of the frame (for example along between 50 and 80% of the non-attached interface between the diaphragm and the frame and/or over more than 80% of the non-attached interface) may be substantially perpendicular to the frame (for example ranging between 0 to 5 degrees of perpendicular and/or between 5 and 15 degrees and/or between 15 and 30 degrees).

Optionally the length (for example the longitudinal axis and/or the maximum and/or mean wall height) of the frame may be short (for example ranging between 5 to 15 and/or between 15 to 20 mm and/or between 20 to 25 mm and/or between 25 to 30 mm and/or between 30 to 45 mm and/or between 45 to 70 mm). For example the axial length of the frame may range between 20 to 30% of its outer perimeter and/or between 30 to 40% and/or between 40 to 50% of its outer perimeter (for example the outer perimeter may be defined as the perimeter of the frame, for example its circumference, at the ventricle end and/or the minimum perimeter of the orifice in which the frame is to be inserted. For a tricuspid prosthesis, the frame is optionally short enough to avoid blocking the right ventricular outflow tract (RVOT). Optionally the frame is long enough for the diaphragm to reliably close against the inner walls of the orifice.

In some embodiments, the diaphragm may include a smooth curved dome shape, for example an ellipsoid dome optionally including a cylindrical section. The volume of the diaphragm would optionally be for example $\pi ab(h+2c/3)$ where a and b are the long and short radii of the cross section and h is the height of the cylindrical portion and c is the height of the ellipsoid section. For example a circular dome of radius $a=b=17$ mm and height $c=25$ mm would have a volume of approximately 15 ml. If a diaphragm had for example an additional right circular cylindrical section of height 5 mm it would have a volume of approximately 20 ml. For a large regurgitation volume and/or large surface area of the diaphragm the length of the frame may be increase (for example in order to improve closing of the valve and/or avoid the inversion of the diaphragm).

In some embodiments, the frame may have an irregularity. For example for a tricuspid prosthesis, the frame may be flattened along a length of the perimeter ranging between 0.5 to 2 mm and/or between 2 to 6 mm and between 6 to 10 mm. For example the flattening may be in a region where the frame comes near the septal wall of the heart. For example, the flattening may be in the vicinity of a septal leaf ventricle extension.

An aspect of some embodiments relates to a delivery system for a prosthetic valve. For example, the delivery system may include a guide wire and/or a hollow tube through which the guide wire passes. The delivery system may optionally include a knurl and/or tip. In some embodiments, tip may be blunt. For example blunt enough to prevent damage to the vessel wall. The hollow tube is optionally threaded into the tip. Optionally the guide wire locks the tube and the tip together. For example, the guide wire may prevent the hollow tube from disconnecting from the guide wire and/or prevents damage to vessel walls as the device is navigated to the treatment area. For example the guide wire may pass through an opening in the knurl. While guide wire passes through the knurl the hollow tube and/or the prosthesis are optionally be prevented from being released. Optionally, the knurl may have a blunt shape, for example to prevent damage to the vessel wall. The guide wire and/or tube is optionally is threaded through the knurl. Threading the wire and/or tube through the knurl optionally locks the hollow tube and/or knurl and/or wire together.

In some embodiments, the guide wire and/or hollow tube may pass through a channel of the prosthesis. In some embodiments an extender (for example including a shaft and/or a wire and/or a tube and/or a chord) may pass through a second channel of the prosthesis. For example the extender may be connected to and/or retain the knurl.

In some embodiments, objects passing through multiple channels of the prosthesis may distribute the forces on the prosthesis. For example, passing objects through multiple channels may distribute forces more evenly. Alternatively or additionally passing objects through multiple channels may balance and/or reduce stresses on a vulnerable part of the prosthesis. For example, passing the guide wire through a first channel of a peripheral flow valve and an extender through a second channel may protect a delicate central diaphragm from unbalanced forces.

In some embodiments, the prosthesis may be positioned in the heart by transcatheter and/or percutaneous delivery.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

States of a Prosthesis

Referring now to the drawings, FIG. 1 is a state diagram of a prosthetic valve and/or delivery system in accordance with some embodiments. For example, the valve and delivery system may be assembled and/or inserted into a patient (for example using a catheter and/or percutaneous delivery. In some embodiments, deployment of the prosthesis may include placing the prosthesis and/or orienting the prosthesis and/or attached the prosthesis to the native tissue. Optionally after delivery the delivery system is released and/or retrieved.

In some separate components 102 of the prosthesis and/or delivery system may be assembled. For example a guide wire and/or a hollow tube and/or an extender may be reversible inserted 104 through one or more flow channels of the prosthesis. A delivery knurl is optionally attached to the distal portion of the extender. For example a hollow tube may be inserted into one channel of the prosthesis and/or a guide wire may be inserted through the hollow tube. For example an extender may be inserted through the one channel and/or through a second channel. In some embodiments the distal end of the guide wire and/or the hollow tube may be reversibly threaded 106 through an opening in the delivery knurl.

In some embodiments, the prosthesis may have a collapsed 108 state. For example the prosthesis may be reversibly collapsed over the hollow tube, guide wire and/or extender. Optionally in the collapsed 108 state, the prosthesis may be reversibly fit into a catheter 110, for example, for delivery to an affected organ.

In some embodiments, the valve and/or the catheter may be guided 111 to the implantation site.

In some embodiments, the prosthesis may be partially deployed 112 from the catheter. For example in the partially deployed 112 state, a ventricle anchor may be deployed from the catheter. In some embodiments, deployment of an anchor inside a patient may be irreversible and/or difficult to reverse. Alternatively or additionally, deploying of an anchor may be reversible. The ventricle anchors are optionally used to reversibly guide to prosthesis to a position oriented 114 to the native structure (for example for a valve prosthesis to the native valve).

In some embodiments, the prosthesis may be released 115 from the catheter opened into an expanded 116 state. The expanded 116 prosthesis may be attached 118 to the native tissue. Attachment may include, for example placing anchors and/or coapting a ring to native tissue. Optionally expansion and/or attachment inside a patent may be irreversible and/or difficult to reverse. Alternatively or additionally expansion and/or attachment may be reversible.

In some embodiments, a valve prosthesis may have an open 120 and/or a closed 122 state. For example, a tricuspid valve prosthesis may be open 120 during diastole and/or closed 122 during systole.

A Prosthesis

Figure 2A:
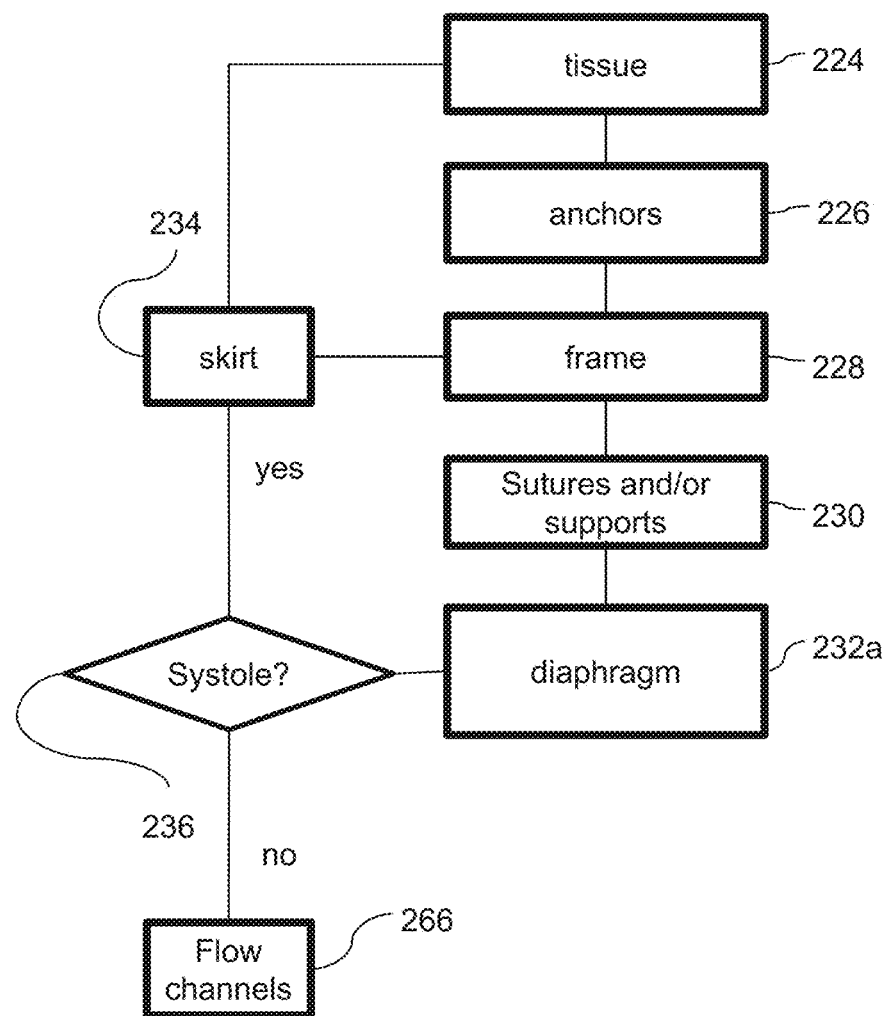
FIGS. 2A and 2B are block diagrams of prosthetic valves in accordance with some embodiments.

Referring now to the drawings, FIG. 2A is a block diagram of a prosthetic valve in accordance with some embodiments. In some embodiments, the prosthesis optionally includes a frame 228 that is attached to native tissue 224. Optionally frame 228 is attached to the tissue 224 by means of one or more anchors 226 and/or by means of a coaptive skirt 234. The frame is optionally attached to a diaphragm 232a. For example the frame may be attached to the diaphragm 232a via sutures (for example on the periphery of the frame) and/or one or more supports and/or a coaptive skirt 234. For example, for a tricuspid valve prosthesis, the diaphragm may close against the frame during systole, impeding flow through the valve and/or the diaphragm may be distanced from the frame during diastole opening one or more peripheral flow channels 266.

Optionally diaphragm 232a includes a pericardium. Optionally diaphragm 232a includes one or more leaflets. Optionally the thickness of diaphragm 232a ranges between 0.1 to 0.5 mm.

Figure 2B:
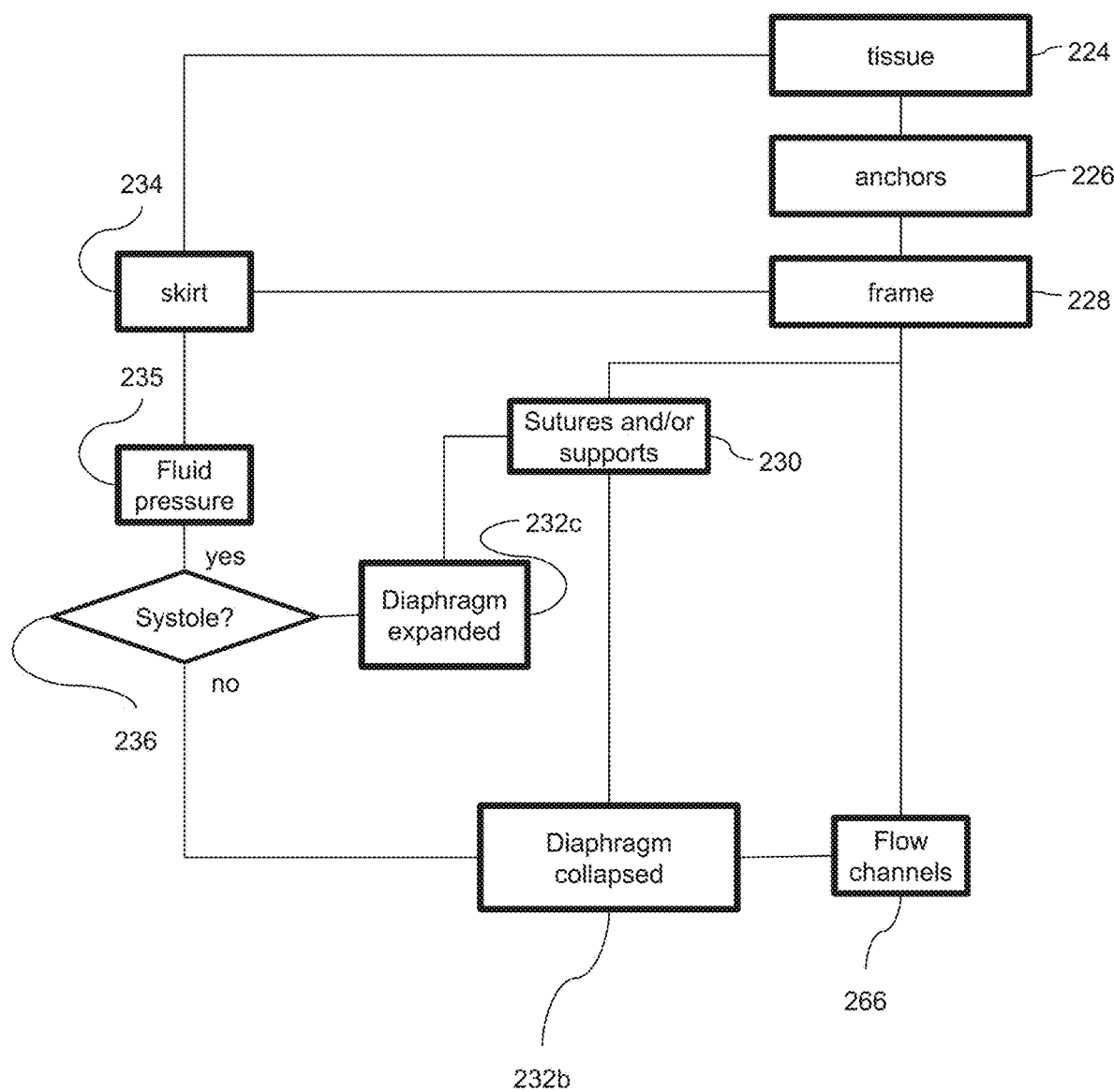

Referring now to the drawings, FIG. 2B is a block diagram of a prosthetic valve in accordance with some embodiments. In some embodiments, the prosthesis optionally includes a frame 228 that is attached to native tissue 224. Optionally frame 228 is attached to the tissue 224 by means of one or more anchors 226. The frame is optionally attached to a diaphragm (for example, an attached portion of the diaphragm may be attached to a portion of the frame in an expanded 232c and/or a collapsed 232b state). Optionally, the frame may be attached to the diaphragm on the periphery of the orifice, for example via sutures 230 and/or one or more supports and/or a skirt 234.

In some embodiments, the diaphragm in the expanded state 232c may close the valve. Optionally, an unattached portion of the diaphragm in the expanded state 232c may press against frame 228 and/or a skirt 234. For example a tricuspid prosthesis diaphragm may be in an expanded state 232c during systole 236. Closing the valve optionally impedes flow through the valve. Optionally, fluid pressure 235 may supply a force pushing the diaphragm in an expanded state 232c against the frame. Optionally, during diastole (for example not during systole 236) the diaphragm in a collapsed state 232b may be distanced from the frame. For example, fluid pressure 235 may distance the diaphragm in the collapsed state 232b from frame 228. Distancing the diaphragm in the collapsed state 232b from the frame optionally opens one or more peripheral flow channels 266. For example, flow channels 266 may be located between frame 228 and an unattached portion of the diaphragm in the collapsed state 232b.

A Delivery System

Figure 3:
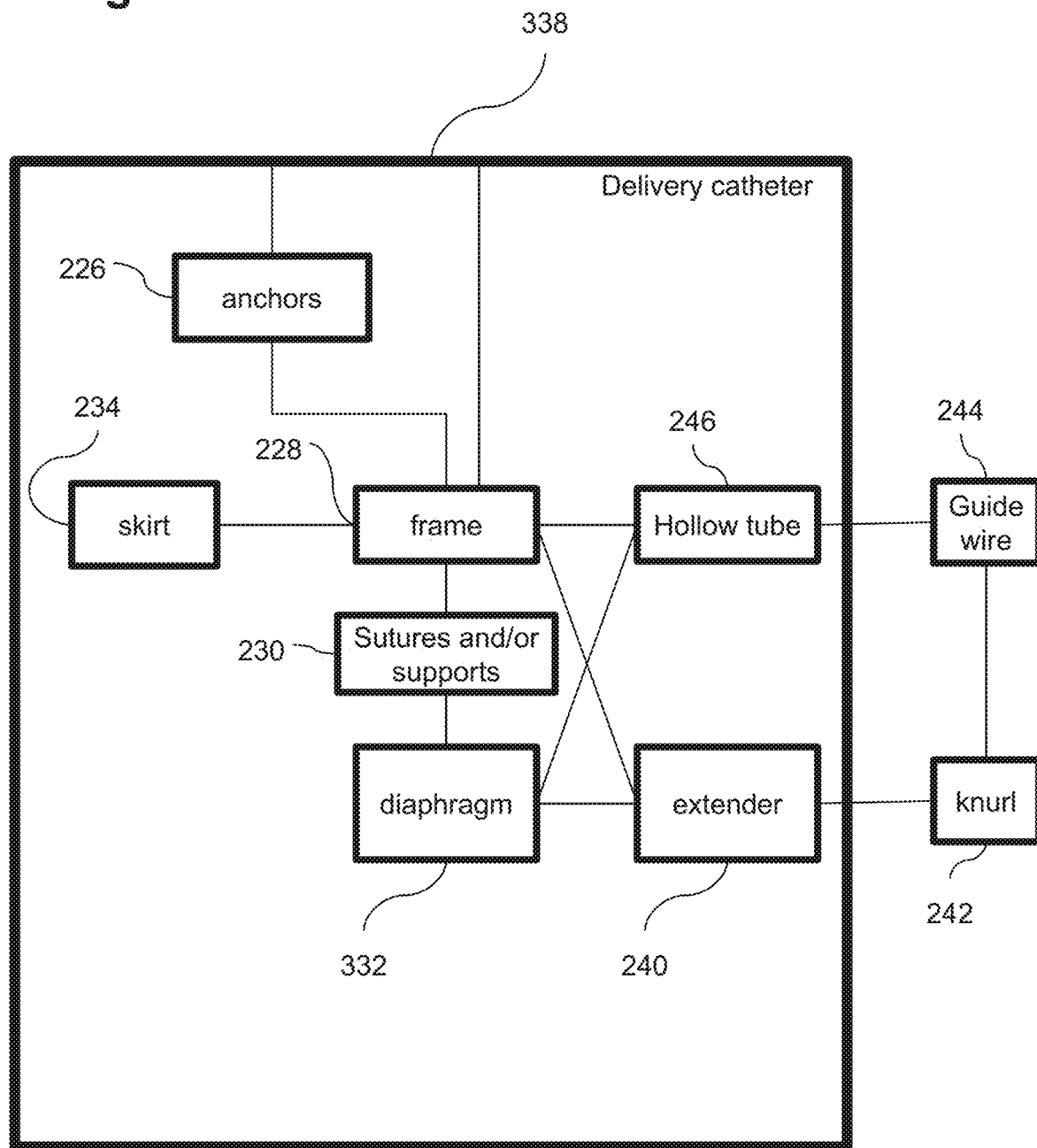
FIG. 3 is a block diagram of a prosthetic valve and/or a delivery system in accordance with some embodiments.

FIG. 3 is a block diagram of a prosthetic valve and/or a delivery system in accordance with some embodiments. Optionally a delivery system is used to position and/or deploy a prosthesis in a patient. For example, the delivery system may include a knurl 242 optionally mounted on an extender 240. The knurl and/or extender optionally prevent premature release of the prosthesis and/or a hollow tube 246.

In some embodiments, the prosthesis is delivered to a treatment zone using a catheter 338. Optionally a hollow tube 246 and/or a guide wire 244 and/or an extender 240 are strung from the proximal end of the catheter, through one or more flow channels 266 of the prosthesis (for example between a frame 228 of the prosthesis and a diaphragm 332 of the prosthesis). The prosthesis may for example be collapsed around the tube 246 and/or a guide wire 244 and/or an extender 240 and/or inserted into the catheter. Extender 240 and/or guide wire 244 optionally extend out of the distal and of catheter 338. Extender optionally holds a knurl 242 distal to catheter 338. For example, knurl 242 may be a delivery tip of catheter 338. Optionally, guide wire 244 passes through an opening in knurl 242. For example, the distal end of guide wire 244 may protrude from a distal opening in knurl 242. Optionally guide wire 244 may be used to guide catheter 338 to a treatment location. Then guide wire 244 and/or tube 246 and extender 240 and/or knurl 242 may be retrieved (for example using catheter 338) from the treatment location.

Functioning of a Prosthetic Valve

Figure 4:
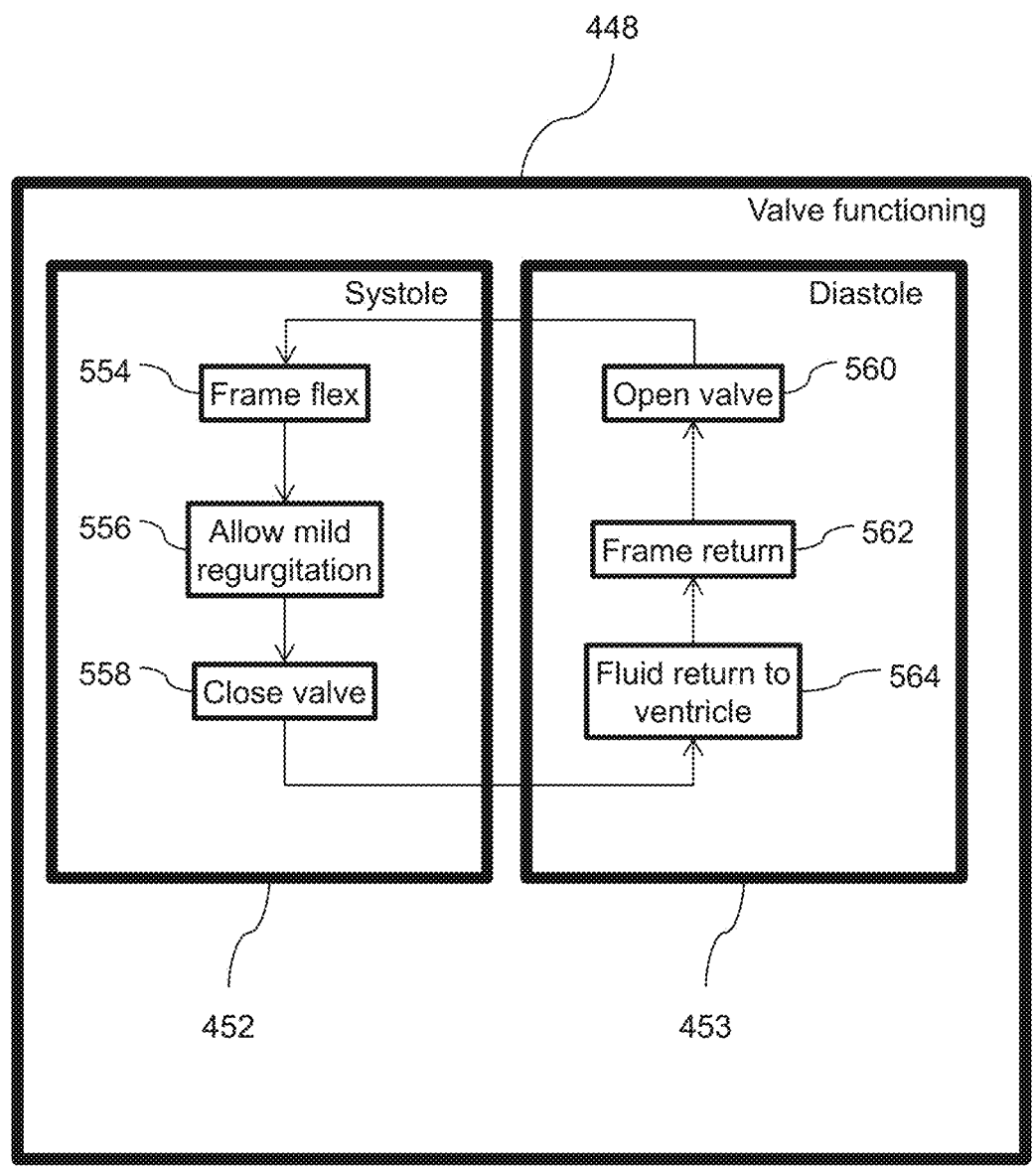
FIG. 4 is a flow chart illustrating functioning of a prosthetic valve in accordance with some embodiments.

FIG. 4 is a flow chart illustrated functioning 448 of a prosthetic valve in accordance with some embodiments. In some embodiments, the valve may permit the annulus to flex while controlling flow through a channel, an orifice and/or annulus. For example the valve may permit one way flow. Optionally, the valve allows mild and/or controlled regurgitation.

In some embodiments, a frame of the valve may take the form of a native annulus. For example as the annulus flexes the frame may flex and/or elastically deform. For example, the ratio of lengths of an axis of the frame and/or annulus before and after deformation may range between 9:10 to 4:5 and/or 4:5 to 2:3 and/or 2:3 to 1:2 and/or 1:2 to 1:4. For example, in the case of a tricuspid valve prosthesis, during diastole 453 the frame may have a nearly circular cross section. Optionally, during systole 452 the frame may flex 554 to an oval shape (for example with a ratio of lengths of a principle and secondary axis ranging between 9:10 to 4:5 and/or 4:5 to 2:3 and/or 2:3 to 1:2 and/or 1:2 to 1:4).

In some embodiments, the valve may close and/or inhibit 558 flow in one direction. For example in the case of a tricuspid prosthetic flow may be blocked and/or inhibited from the right ventricle to the right atrium. Optionally a free edge of the diaphragm may be held pressed to the periphery of the orifice (for example along an inner wall of the frame)

by fluid pressure and/or close 558 the valve. Optionally an attachment between the frame and the diaphragm may prevent the diaphragm from being pushed through the orifice.

In some embodiments the valve may allow 556 controlled and/or mild regurgitation. For example, a valve that is connected to a chamber may allow 556 regurgitation of a volume ranging between 1 to 10% of the volume of the chamber and/or between 10 to 15% and/or between 15 to 25% and/or between 25 to 40%. For example in the case of a tricuspid prosthetic, the chamber may be the right ventricle. For example, limited regurgitation flow may be permitted from the right ventricle in the direction of the right atrium. For example in the case of a tricuspid prosthetic, the regurgitated volume may range between 1 to 10 ml and/or between 10 to 15 ml and/or between 15 to 25 ml and/or between 25 to 40 ml.

In some embodiments, regurgitated fluid may be returned 564 to the original chamber. For example, for a tricuspid prosthetic some or all (for example ranging from 10 to 50% and/or from 50 to75% and/or from 75 to 100%) of the fluid regurgitated from the ventricle during systole 452 may be returned back to the ventricle during diastole 453. For example, regurgitated fluid may be returned 564 to the ventricle at the beginning of diastole 453.

In some embodiments the shape of the valve may open 560 for example during diastole allowing flow from a right atrium to a right ventricle during diastole. A frame and/or the annulus of flow may be reformed 562. For example in a tricuspid prosthetic, the frame and/or tricuspid annulus may reform to an approximately circular cross section during diastole 453.

Deployment

Figure 5:
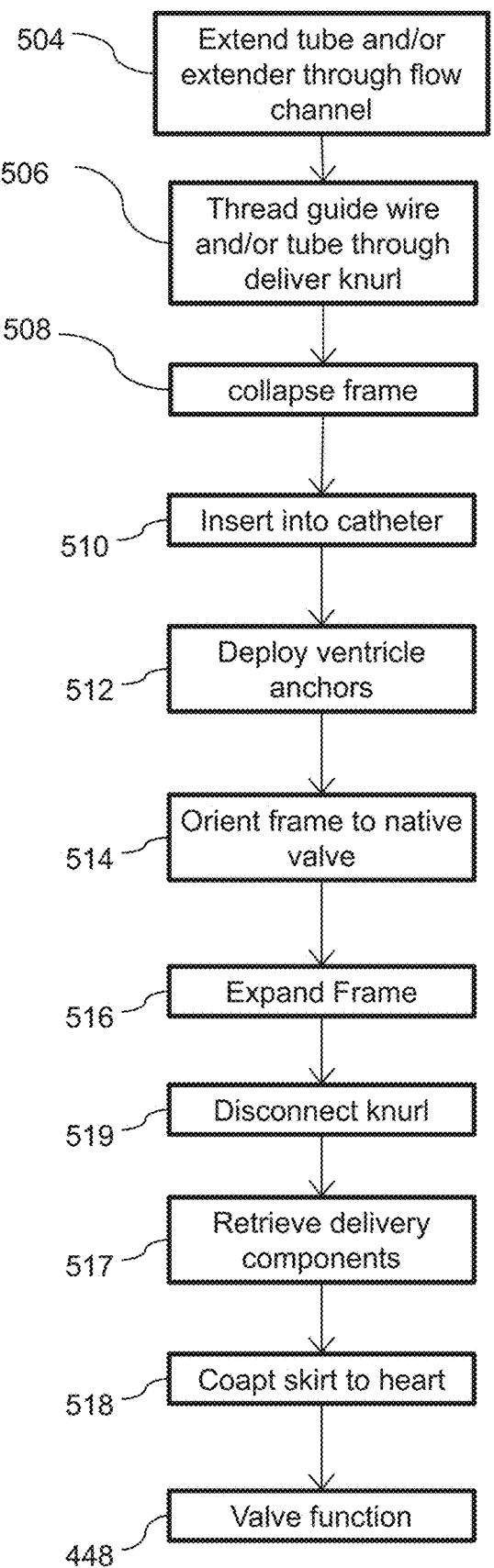
FIG. 5 is a chart illustrating deployment of a prosthetic valve in accordance with some embodiments.

FIG. 5 is a flow chart illustrated deployment of a prosthetic valve in accordance with some embodiments. In some embodiments a hollow tube may be extended 504 through a first flow channel of the prosthesis and/or an extender may be extended 504 through another channel. Alternatively and/or additionally, both the tube and/or the extended may be extended 504 through the same channel. For example a knurl may be supported on the distal side of the prosthesis by the extender. Optionally a guide wire and/or the hollow tube and/or the extender may be threaded 506 through the tube and/or an opening in the knurl. For example the tip of the guide wire may extend distally to the knurl.

In some embodiments, the frame may be collapsed 508 around the tube and/or the extender and/or the frame, tube, extender, knurl and/or guide wire may be inserted 510 into a catheter. Optionally the catheter may be used to deliver the prosthesis and/or delivery system to the treatment location (for example the right ventricle of the heart). In the heart, the ventricle stabilizers may optionally be deployed 512. Optionally the stabilizers and/or the prosthesis may be oriented 514 to the native valve and/or orifice. For example, the ventricle stabilizers may be fit over the native leafs of the valve.

In some embodiments, once the stabilizers are in place, the frame may be expanded 516. For example, expanding 516 the frame may include attaching the frame to heart tissue. With the frame attached to the heart, the guide wire and/or tube and/or extender may be pulled 519 out of and/or disconnected from the delivery knurl and the guide wire, knurl, extender and/or catheter may be retrieved 517 from the patient. Optionally a skirt and/or ring may be coapted 518 to the heart of the patient. One the valve is in place it may optionally begin to function 448.

Views of Embodiments of a Tricuspid Prosthetic

Figure 6:
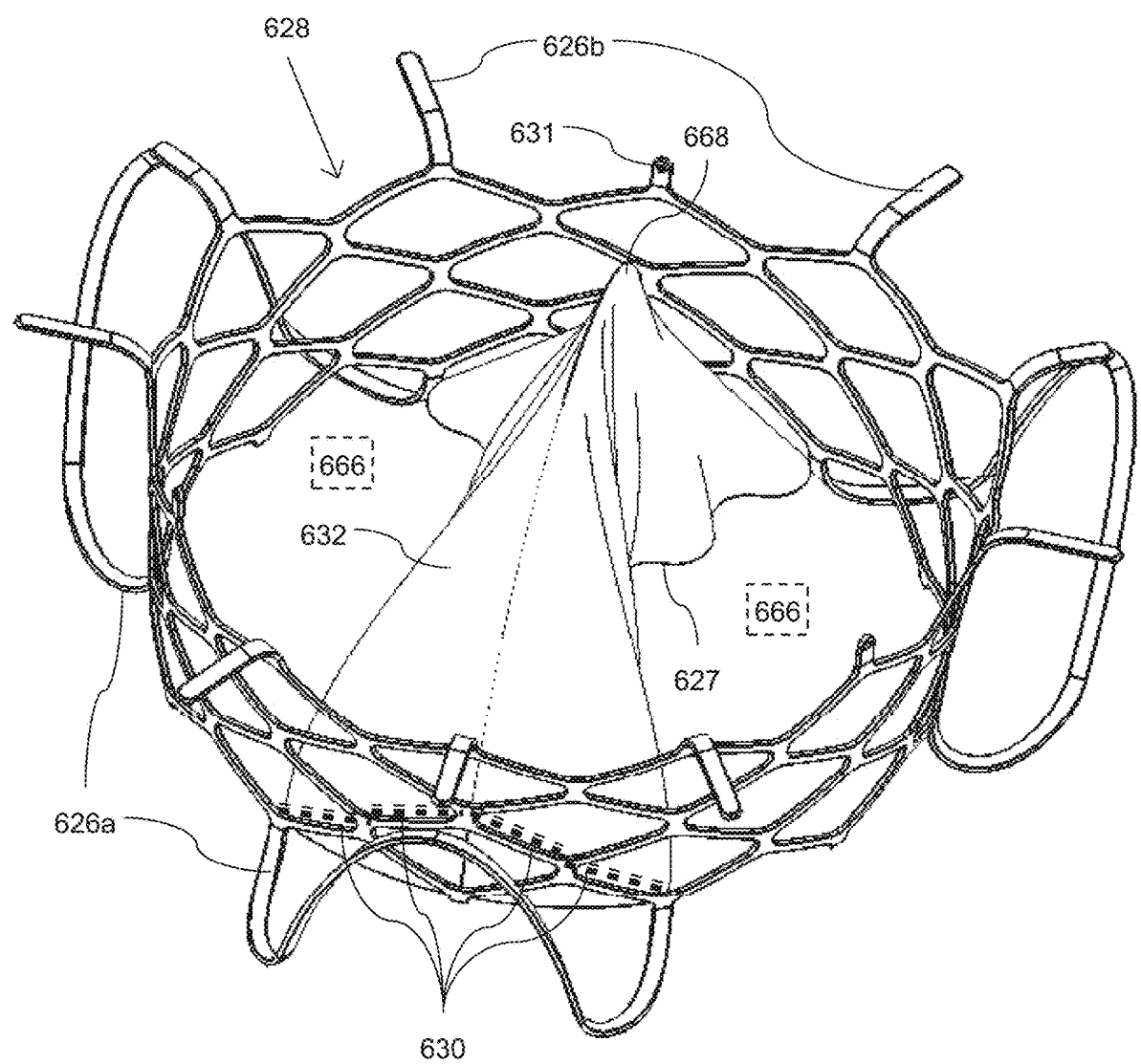
FIG. 6 is a perspective illustration of a prosthetic valve with the frame expanded and the valve open in accordance with some embodiments.

FIG. 6 is a perspective illustration of a prosthetic valve with the frame expanded and the valve open in accordance with some embodiments. In some embodiments a tricuspid prosthetic includes a central diaphragm 632. Diaphragm 632 is optionally attached along part of the periphery of a tricuspid annulus to a frame 628. For example attachment may be by means of sutures 630. Optionally diaphragm 632 includes an apex 668. Optionally apex 668 is located upstream of a frame 628 of the prosthesis.

In some embodiments in the open configuration diaphragm 632 is collapsed and/or folded and/or pushed inward leaving peripheral flow channels 666*a-b*. For example flow channels 666*a-b* may be between diaphragm 632 and the tricuspid annulus and/or frame 628 and/or an optional skirt. For example, flow channels 666*a-b* may be located on opposite sides of diaphragm 632. Optionally, the sum of the cross sectional areas of the peripheral flow channels 666*a-b* may range from 10 to 30% and/or 30 to 50% and/or from 50 to75% and/or from 75 to 100% of the cross section of the tricuspid annulus. For example, in some embodiments, the area flow channels in the open valve may be approximated by slightly (0-20%) less than the area of two segments of the circle formed by chords connected the ends of the attached portion of the periphery. For example, for an approximately circular frame of diameter 45 mm having a attachment length of 5 mm, the open area of the flow channels may be between 80 to 95% of the area of the orifice. For example, for an approximately circular frame of diameter 45 mm having a attachment length of 2.5 mm, the open area of the flow channels may be between 85 to 96% of the area of the orifice.

In some embodiments a prosthetic valve may include a coaptation band. For example the edge of the coaptation band may coapt with the back wall of the heart tissue. For example the coaptation band may coapt with the inner wall of the ventricle and/or the inner wall of the atrium. Optionally may include a coaptation band. For example, the width of the coaptation band may range between 0.1 to 2 mm and/or between 2 to 4 mm and/or between 4 to 6 mm and/or between 6 to 10 mm and/or between 10 to 15 mm. Optionally the coaptation band may be connected to a skirt may that covers the inner surface of the frame. For example the skirt may cover an area ranging from 0 to 25% and/or from 25 to 50% and/or from 50 to 75% and/or from 75 to 100% of the inner walls of the frame and/or the orifice. Optionally the skirt may be attached to the frame. For example, the skirt may be sutured to the frame. For example the skirt and/or the coaptation band may be made of biocompatible fabric and/or bovine/porcine pericardium.

In some embodiments diaphragm 632 may be attached to a periphery of the tricuspid annulus and/or frame 628. For example attachment may be by means of sutures 630. The attachment optionally holds diaphragm 632 at least partially expanded and/or open during diastole. Attachment is optionally along struts of frame 628. Alternatively or additionally diaphragm 632 may be sutured to the skirt. For example, the length of attachment and/or suture lines (suturing the leaflet to the frame and/or the skirt and/or the periphery of the orifice) may range between 0.1 to 1% and/or between 1% to 3% and/or between 3% to 5% and/or between 5% to 7% and/or between 7% to 10% and/or between 10% to 15% and/or between 15% to 30% and/or between 30% to 50% of the perimeter of the entire orifice for example the tricuspid annulus. Optionally, there may be one or more suture lines. For example there may be 2 or 3 suture lines. Optionally, the leaflet is sutured not only along the perimeter of the frame but also in axial direction. Sutures may hold a portion of diaphragm 632 partially expanded and/or open during diastole.

For example at the beginning of systole, flow into the portion of diaphragm 632 that was expanded and/or open during diastole may cause diaphragm 632 to fill up with blood. In some embodiments, when diaphragm 632 fills, a free edge 627 of diaphragm 632 may be pushed against the periphery of the orifice and/or frame, optionally blocking back flow (for example as illustrated in FIGS. 6, 8B, 9B, 9D and/or 9E). Sutures may optionally be made of a biocompatible material. Optionally the free edge 627 of diaphragm 632 may extend beyond (for example downstream into the ventricle end of) the frame 628. For example, free edge 627 may extend beyond the frame where there are no sutures. The orifice may in some cases flex to a non-circular shape (for example an oval and/or crescent shape) during systole, the suture lines are optionally positioned substantially perpendicular to the minor axis of the non-circular shape (for example as illustrated in FIGS. 9B and/or 10).

Optionally frame 628 may be made of a self expanding and/or shape memory material, for example nitinol. In some embodiments the axial length of the frame may range for example between 10 to 20 mm and or between 20 to 30 mm and/or between 30 to 50 mm. Frame 628 may be short in a way it would extend into the right ventricle for only a few millimeters for example between 1 and 5 mm and/or between 5 and 10 mm and/or between 10 and 30 mm. For example the frame may not obstruct the right ventricular outflow tract (RVOT).

In some embodiments frame 628 may include one or more atrial extensions 626b. Extensions 626b optionally include anchors and/or stabilizers. For example an atrial extension 626b may be bent to be approximately parallel (for example between +5 to −5 degrees and/or between +5 to +20 degrees and/or between −5 to −20 degrees) to frame cross section. Atrial extension 626b optionally extends outward between 0.5 to 2 mm and/or between 2 to 8 mm and/or between 8 to 12 mm and/or between 12 to 20 mm radially. Frame 628 optionally includes one or more delivery barbs 631. For example a delivery barb may be used to connect to a string for controlling positioning of the prosthesis during delivery.

In some embodiments frame 628 may include one or more ventricle extensions 626a. Extensions 626a optionally include anchors and/or stabilizers. Ventricular extensions 626a of the frame are optionally bent backwards towards atrial stabilizers 626b and/or may reach atrial stabilizers 626b. For example extension 626a or 626b and/or stabilizers and/or anchors may press against the native annulus for migration resistance.

In some embodiments the diameter of frame 628 may range for example between 1 to 10 mm and/or between 10 to 15 mm and/or between 15 to 30 and/or between 30 to 45 mm and/or between 45 to 60 mm and/or between 60 to 75 mm. For example the diameter may be defined as the mean unstressed diameter and/or maximum unstressed diameter and/or the minimum unstressed diameter. The axial length of frame 628 may range for example between 5 to 15 mm and/or between 25 to 25 mm and/or between 25 to 60 mm. Frame 628 wall thickness may range for example between 0.1 to 0.2 mm and/or between 0.2 to 0.5 mm and/or between 0.5 to 0.75 mm.

Figure 7:
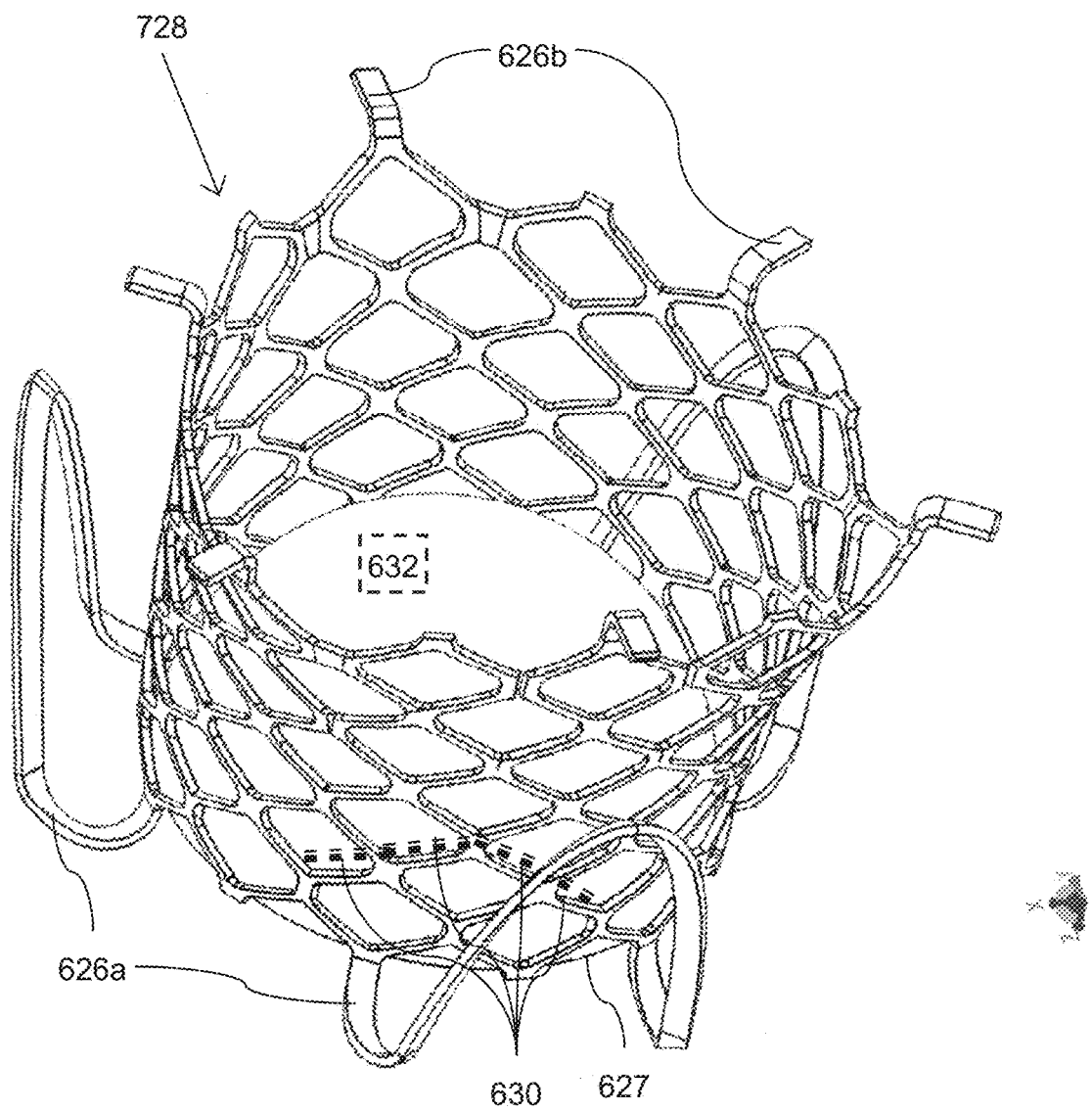
FIG. 7 is a perspective illustration of a prosthetic valve with the frame expanded and the valve closed in accordance with some embodiments.

FIG. 7 is a perspective illustration of a prosthetic valve with the frame expanded and the valve closed in accordance with some embodiments. Frame 728 may optionally have a longer axial length than frame 628.

Figure 8A:
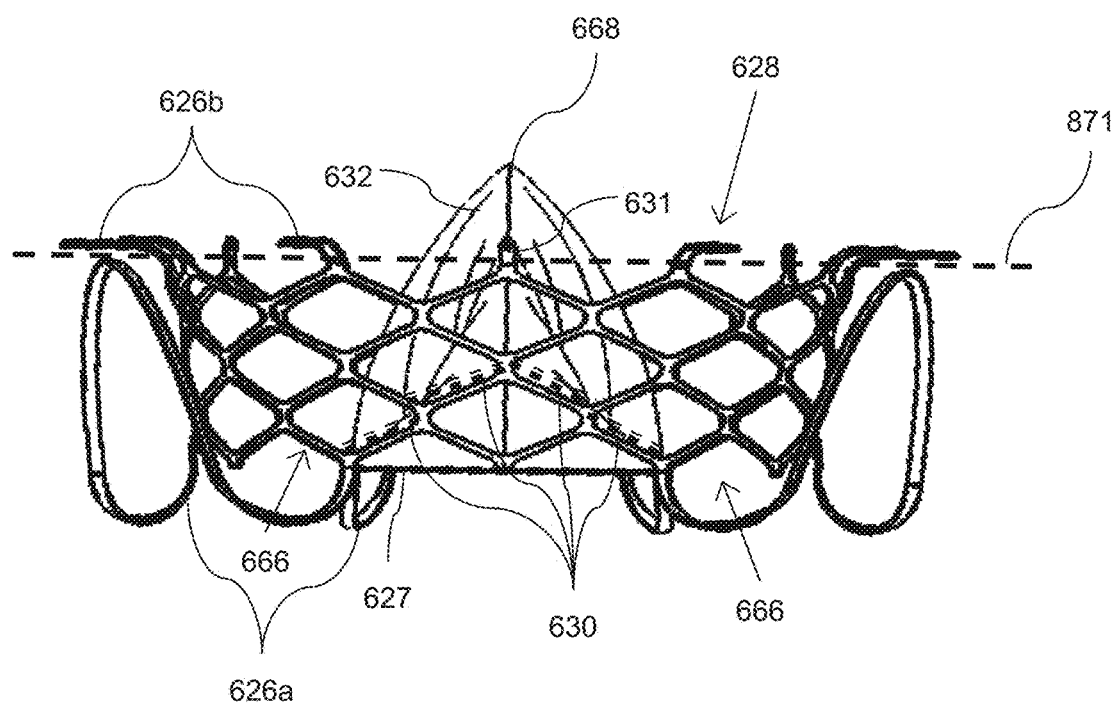
FIG. 8A is a side view illustration of a prosthetic valve with the frame expanded and the valve open in accordance with some embodiments.

FIG. 8A is a side view illustration of a prosthetic valve with the frame expanded and the valve open in accordance with some embodiments. Apex 668 may extend for example a distance ranging from 1 to 10 mm and/or from 10 to 20 mm in the downstream direction into the atrium past the end of frame 628 and/or the tricuspid valve plane 871. The downstream extension is optionally in a free region of the orifice and/or the projection of the orifice where there is no connection and/or sutures between diaphragm 632 and the frame.

In some embodiments the connection between the diaphragm and the frame is near the edge of the diaphragm. For example, the distance between the edge of the diaphragm and the connection to the frame may be less than half the axial length of the frame and/or less than the axial length of the frame and/or less than 1.5 times the axial length of the frame and/or less than 2 times the axial length of the frame. For example, the distance between the edge of the diaphragm and the connection to the frame may be less than 5 mm and/or between 5 to 10 mm and/or less than between 10 to 20 mm and/or between 20 to 30 mm and/or between 30 to 40 mm.

Figure 8B:
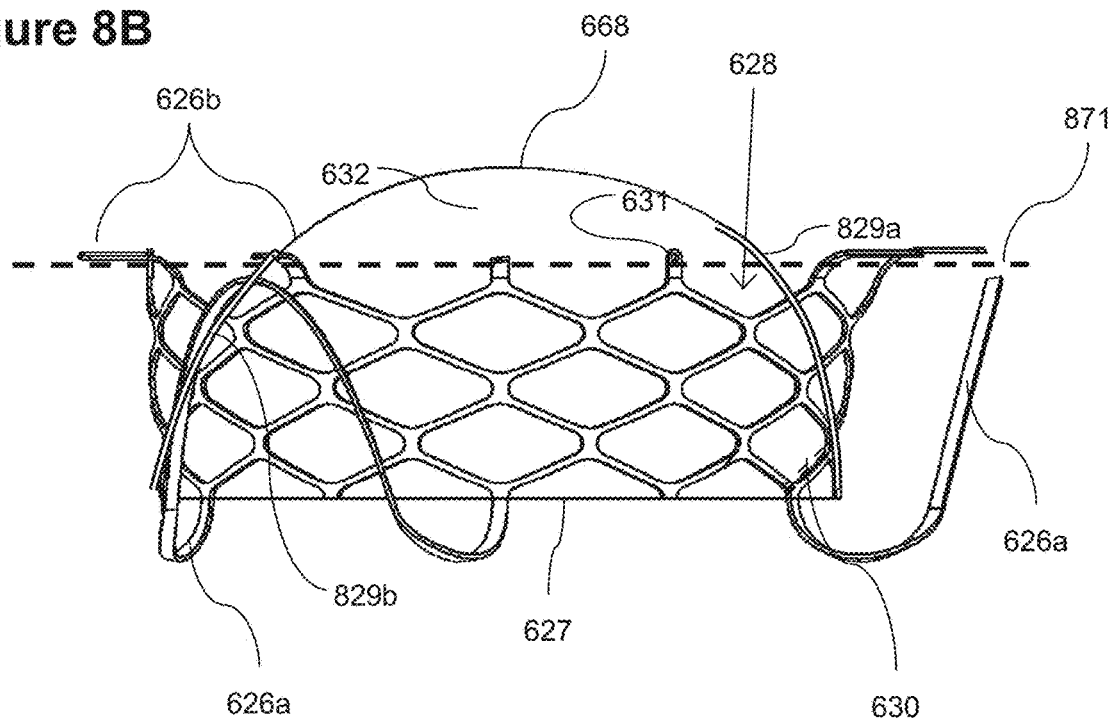
FIG. 8B is a side view illustration of a prosthetic valve with the frame expanded and the valve closed in accordance with some embodiments.

FIG. 8B is a side view illustration of a prosthetic valve with the frame expanded and the valve open in accordance with some embodiments. Along the inner wall of the frame, diaphragm 632 may be nearly tangential to frame 628.

In some embodiments, the diaphragm suturing to the frame forms an almost tangential angle, which may in some embodiments reduce the radial forces acting on the frame during systole. The frame optionally has reduced wall thickness may be more compliant to the valve's shape. For example frame 628 may be flexible enough to deform from a circular shape to a crescent and/or oval shape of the tricuspid annulus during diastole and systole. For example during systole, frame may take a elliptical and/or crescent shape and/or during diastole frame may take a more rounded shape. In some embodiments the reduced wall thickness may result in less force exerted on the septal wall of the heart.

The back pressure generated while the valve closes is optionally translated into forces which are exerted on the frame of the valve. The resolved components (axial and radial) may depend on the angle formed between the frame and the diaphragm. For example when the frame and diaphragm are almost tangential the small angle may lead to small radial and/or axial component.

In some embodiments the radial force applied on the native tricuspid annulus may be much less than the force applied to the frame by for example between 10 to 50% and/or between 50 to 75% and/or between 75 to 90% and/or between 90 to 100%. In some embodiments, the outward force helps prevent valvular leakage. The expanding diaphragm optionally adds volume to the ventricle during systole. Added volume may sometimes reduce pressure overload.

In some embodiments, state, apex 668 may for a smooth and/or convex curve.

Figure 9A:
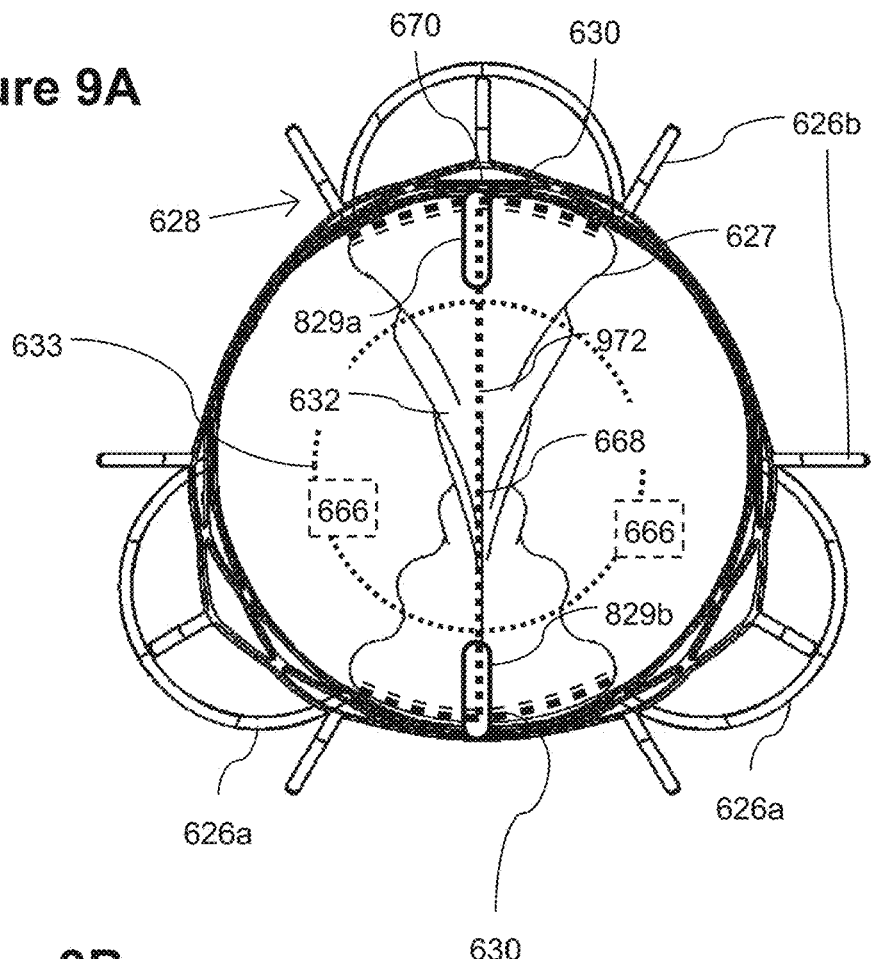
FIG. 9A is a top view illustration of a prosthetic valve with the frame expanded and the valve open in accordance with some embodiments.
Figure 9B:
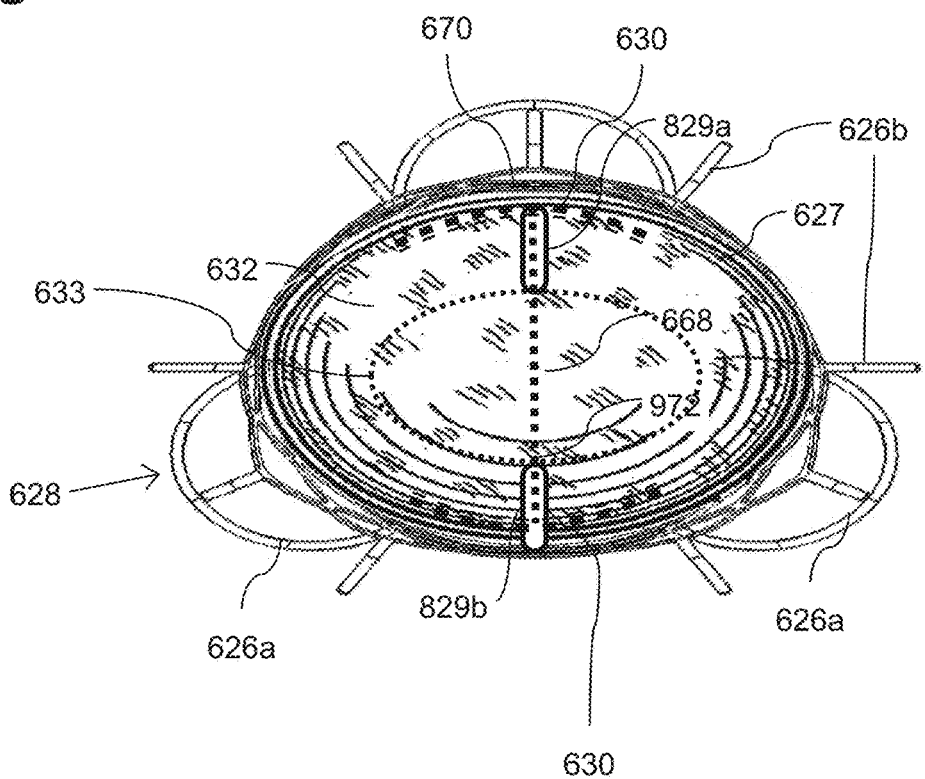
FIG. 9B is a top view illustration of a prosthetic valve with the frame expanded and the valve closed in accordance with some embodiments.

FIG. 9A is a top view illustration of a prosthetic valve with the frame expanded and the valve open in accordance with some embodiments. A flattened portion 670 of frame 628 is optionally near a septal wall of the heart and/or septal ventricle stabilizer 626a that optionally goes over septal leaflet. This feature may optionally reduce the radial force acting on the septal conduction area of a heart.

In some embodiments, the frame 628 may include one or more support elements, for example element 829a and/or support element 829b. Support elements 829a and 829b optionally extend from the periphery of the frame and/or orifice into the orifice and/or into the projection of the orifice into the atrium and/or upstream of the orifice and/or into the inflow zone of the orifice in the atrium. Optionally, support elements 829a and 829b have a cantilever geometry (for example as can be seen in the side view of support elements 829a and 829b illustrated in FIG. 8B), for example only one side of the support element may be attached to the periphery of the frame 628 and/or periphery of the orifice while the other side projects into the flow domain. Optionally support element 829a extend upstream of the peripheral portion of the frame 628 into the projection of the orifice into the atrium and/or upstream of the orifice and/or into the inflow zone of the orifice in the atrium (for example as is seen in FIG. 8B). Optionally support element 829b is surrounded by and/or is surrounded by and/or within the orifice and/or within the peripheral portion of the frame 628. Optionally diaphragm 632 is attached (for example by sutures) to support elements 829a and 829b.

In some embodiments a region 633 of the flow orifice may be free from frame elements and/or rigid supports and/or rigid elements. For example, region 633 of the exemplary embodiment of FIGS. 9A-D does not include any stiff structural elements (for example no metal cross piece and/or no self supporting crosspiece except for the diaphragm itself). Optionally there may be wires and/or stitching that stiffens the diaphragm. For example region 633 is a central portion of the orifice. For example, the cross sectional area of region 633 is approximately 40% of the cross sectional area of the orifice. For example, a frame element free region 633 may include the center of the flow region and/or the center of the frame and/or the center of the orifice. For example, a frame element free region 633 may include an area ranging between 10-30% of the cross sectional area of a frame and/or between 30 to 50% and/or between 50 to 80% and/or between 80 to 100%.

In some embodiments, strengthening may be added along all and/or part of minor axis 972. For example strengthening may include sutures and/or another element.

Figure 10:
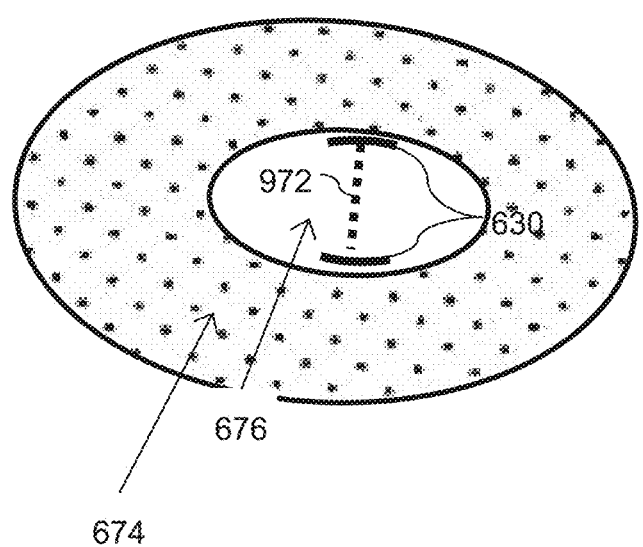
FIG. 10 is an illustration of a tricuspid annulus showing positioning of a prosthetic valve in accordance with some embodiments.

FIG. 9B is a top view illustration of a prosthetic valve with the frame expanded and the valve closed in accordance with some embodiments. For example, in FIG. 9B, frame 628 has flexed to an oval shape. For example the oval shape may conform to native deformation of the tricuspid annulus during systole, for example as illustrated in FIG. 10.

In some embodiments, a prosthetic valve may be designed to function independently of annulus geometries. For example, a valve may be designed to close to backflow to substantially the same degree for an elliptical annulus geometry (for example as illustrated in FIG. 9B) and/or a round annulus geometry (for example as illustrated in FIG. 9D) and/or for a crescent geometry. For example, a valve may close due to pressure forces pushing flexible diaphragm 332 against the inner wall of frame 728. Optionally pressure may be distributed evenly throughout the blood. In some embodiments, the closing may not be dependent on the geometric form and/or non-uniform bending of a solid element. For example under a fluid pressure differential of 10 to 25 mmHg greater pressure on the ventricle side of the valve, the leakage may be within 0 to 2% and/or 2 to 10% and/or 10 to 30% and/or 30 to 50% and/or 50 to 100% for a round annulus and/or for an annulus with an aspect ratio of 3:4. For example under a fluid pressure differential of 10 to 25 mmHg greater pressure on the ventricle side of the valve, the pressure on the annulus and/or the inner wall of frame 728 be evenly distributed within 0 to 2% and/or 2 to 10% and/or 10 to 30% and/or 30 to 50% and/or 50 to 100% for a round annulus and/or for an annulus with an aspect ratio of 3:4.

Figure 9C:
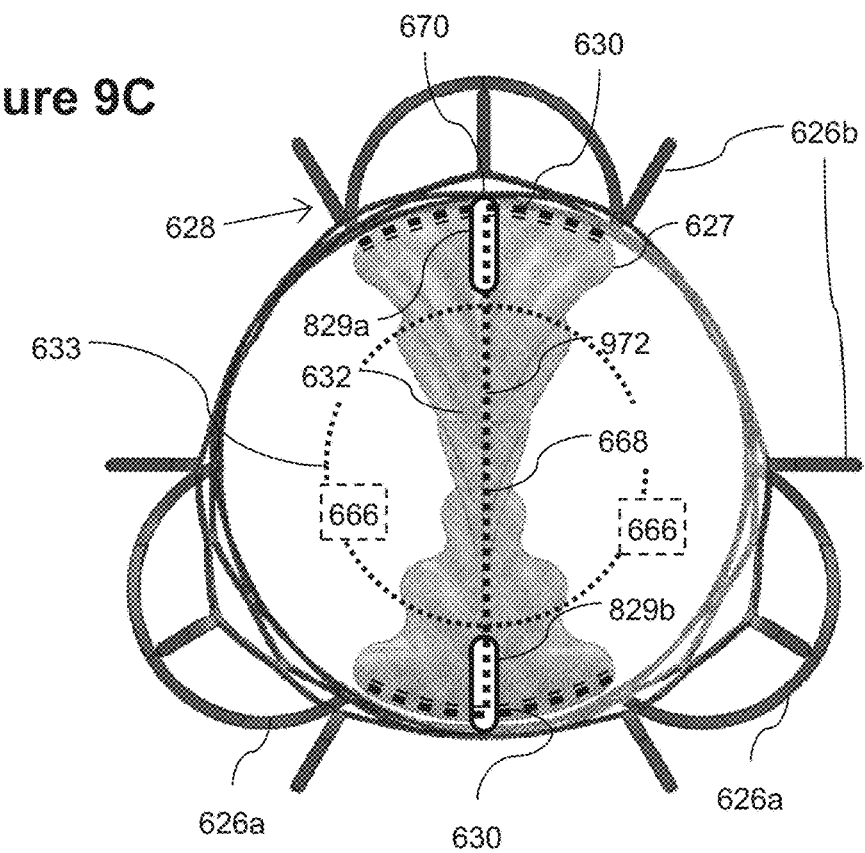
FIG. 9C is a top view illustration of a prosthetic valve with the frame expanded and the valve open in accordance with some embodiments.
Figure 9D:
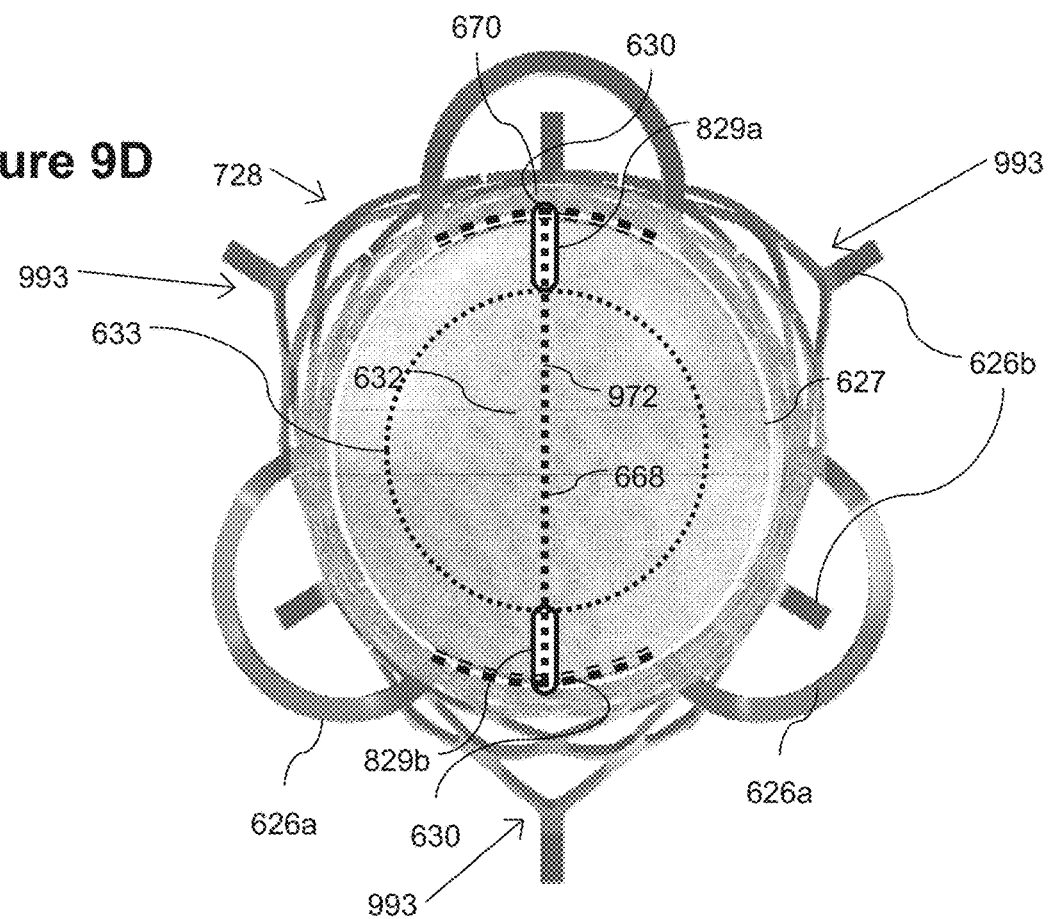
FIG. 9D is a top view illustration of a prosthetic valve with the frame expanded and the valve closed in accordance with some embodiments.

FIG. 9C is a top view illustration of a prosthetic valve with the frame expanded and the valve open in accordance with some embodiments. Optional supports are shown protruding radially inward along axis 972 from the periphery of frame 628.

FIG. 9D is a top view illustration of a prosthetic valve with the frame expanded and the valve closed in accordance with some embodiments. Frame 728 optionally has circular a cross section on ventricle side and triangle cross section on atrial side. The directions of the triangular vertices of the cross section are marked 993.

Figure 9E:
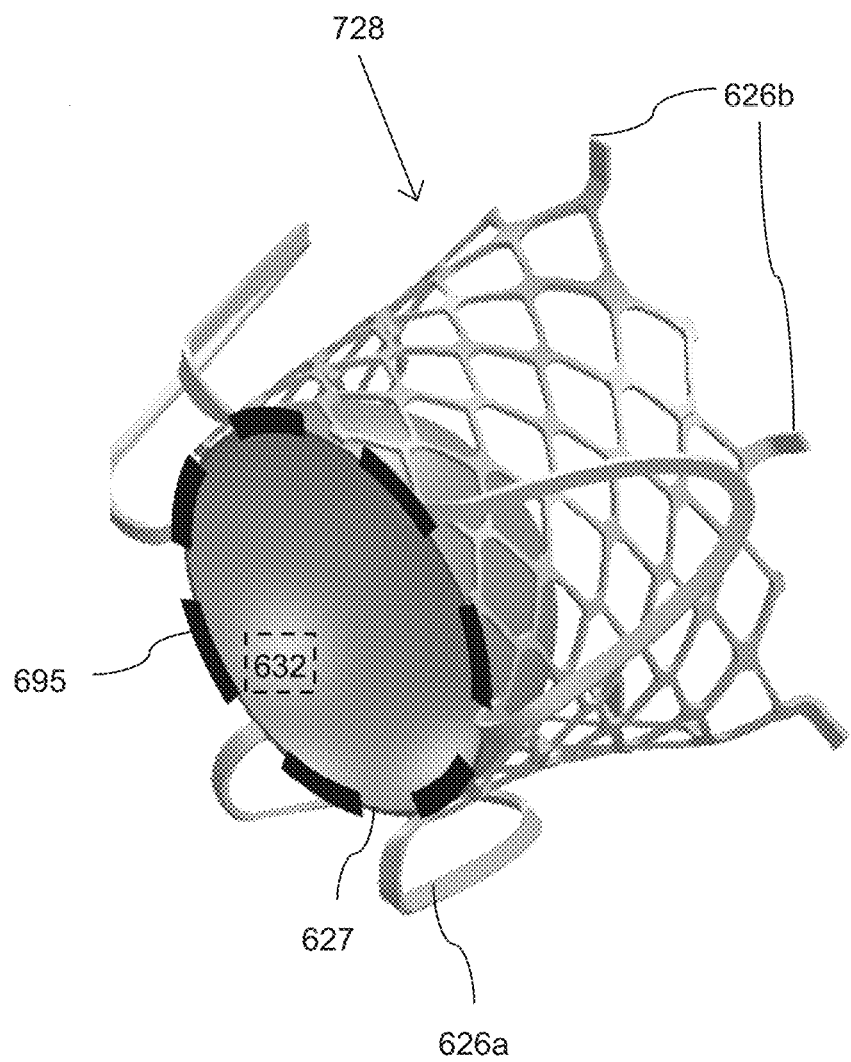
FIG. 9E is a perspective view illustration of a prosthetic valve with the frame expanded and the valve closed in accordance with some embodiments.

FIG. 9E is a perspective view illustration of a prosthetic valve with the frame expanded and the valve closed in accordance with some embodiments. In the expanded state diaphragm 632 optionally has a smooth outer surface. In the expanded state diaphragm 632 optionally has a convex outer surface. For example, the word convex and/or a convex surface may be defined herein in its mathematical sense as a surface having no interior angle greater than 180 degrees and/or as a surface for which any straight line tangent to the surface intersects the surface only once. Examples of diaphragms with smooth, domed and/or convex outer surfaces are illustrated in FIGS. 7, 9B and 9E.

In some embodiments (for example as illustrated by the dashed lines in FIG. 9E) the minimal external perimeter 695 and downstream external perimeter of the frame may be on the downstream end of the frame. Perimeter 695 may not include anchors 626a or extension 626b. Optionally, a frame may have a thin waist and/or flanged ends. In some embodiments the minimal external perimeter may be around the thin waist. For the sake of the current disclosure a perimeter of a frame may be a closed curve that surrounds the flow channel of the frame.

FIG. 10 is an illustration of a tricuspid annulus 674 showing positioning of a prosthetic valve in a flow orifice 676 in accordance with some embodiments. For example, as the native valve flexes to an oval or crescent shape during systole. In some embodiments, suture lines 630 may be positioned perpendicular to the minor axis 972 of the oval. For example the suture lines may be at an angle ranging between 85 and 95 degrees of the short axis, and/or between 75 and 105 degrees.

Figure 11:
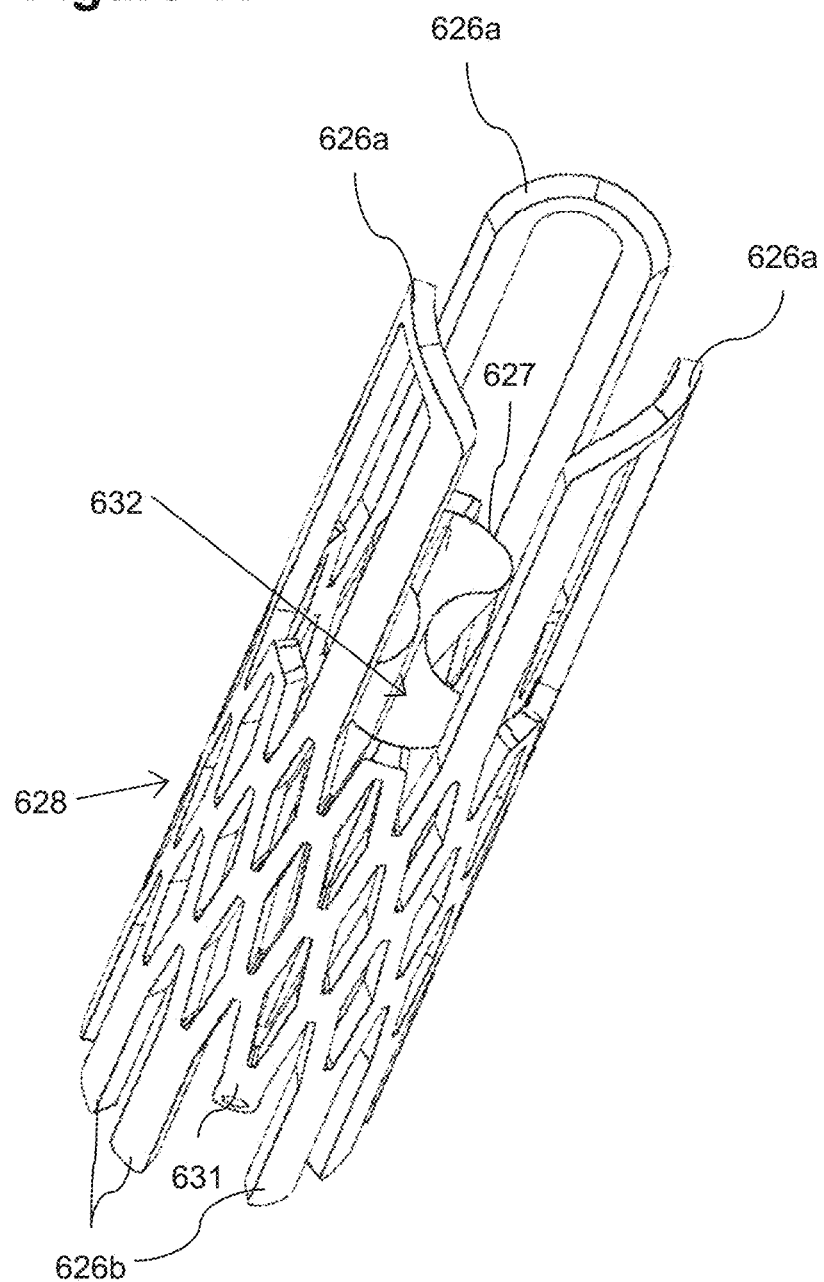
FIG. 11 is a perspective illustration of a prosthetic valve with the frame collapsed in accordance with some embodiments.

FIG. 11 is a perspective illustration of a prosthetic valve with the frame 628 collapsed in accordance with some embodiments. In some embodiments, the prosthetic valve in the collapsed configuration may be delivered through a catheter to a treatment region (for example the right ventricle of the heart).

Figure 12:
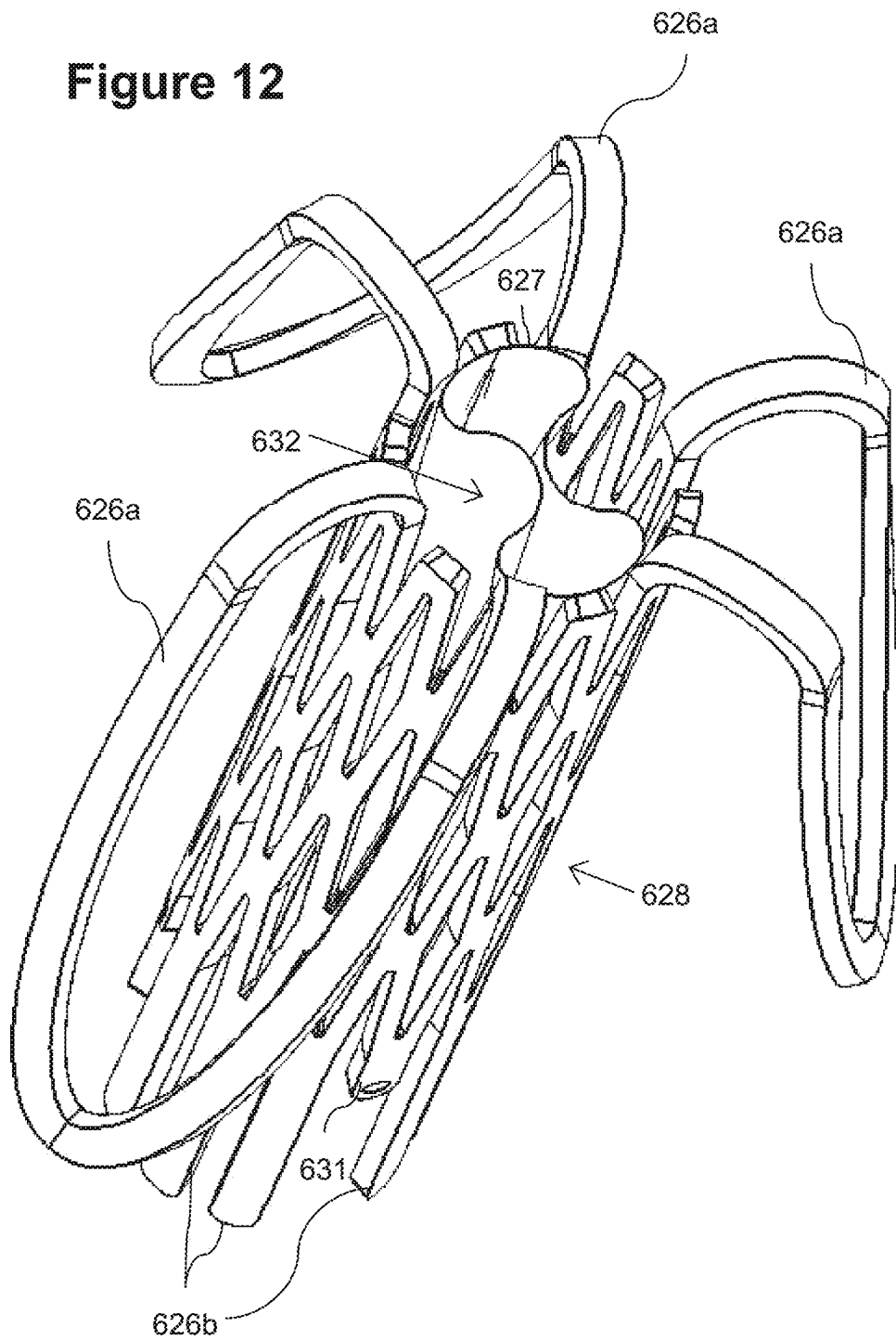
FIG. 12 is a perspective illustration of a prosthetic valve with the frame collapsed and ventricle anchors deployed in accordance with some embodiments.

FIG. 12 is a perspective illustration of a prosthetic valve with the frame 628 collapsed and ventricle anchors 626a deployed in accordance with some embodiments. In some embodiment, when a prosthesis arrives at a treatment site in a catheter, the prosthesis may be partially extended from the catheter and anchors 626a may be deployed. Anchors 626a are optionally used to orient the prosthesis as it is positioned during deployment. For example, anchors 626a may be placed over the native leaves of the tricuspid valve. Once the prosthesis is in place the delivery catheter may be gradually retracted for example leaving the prosthesis in place.

Figure 13:
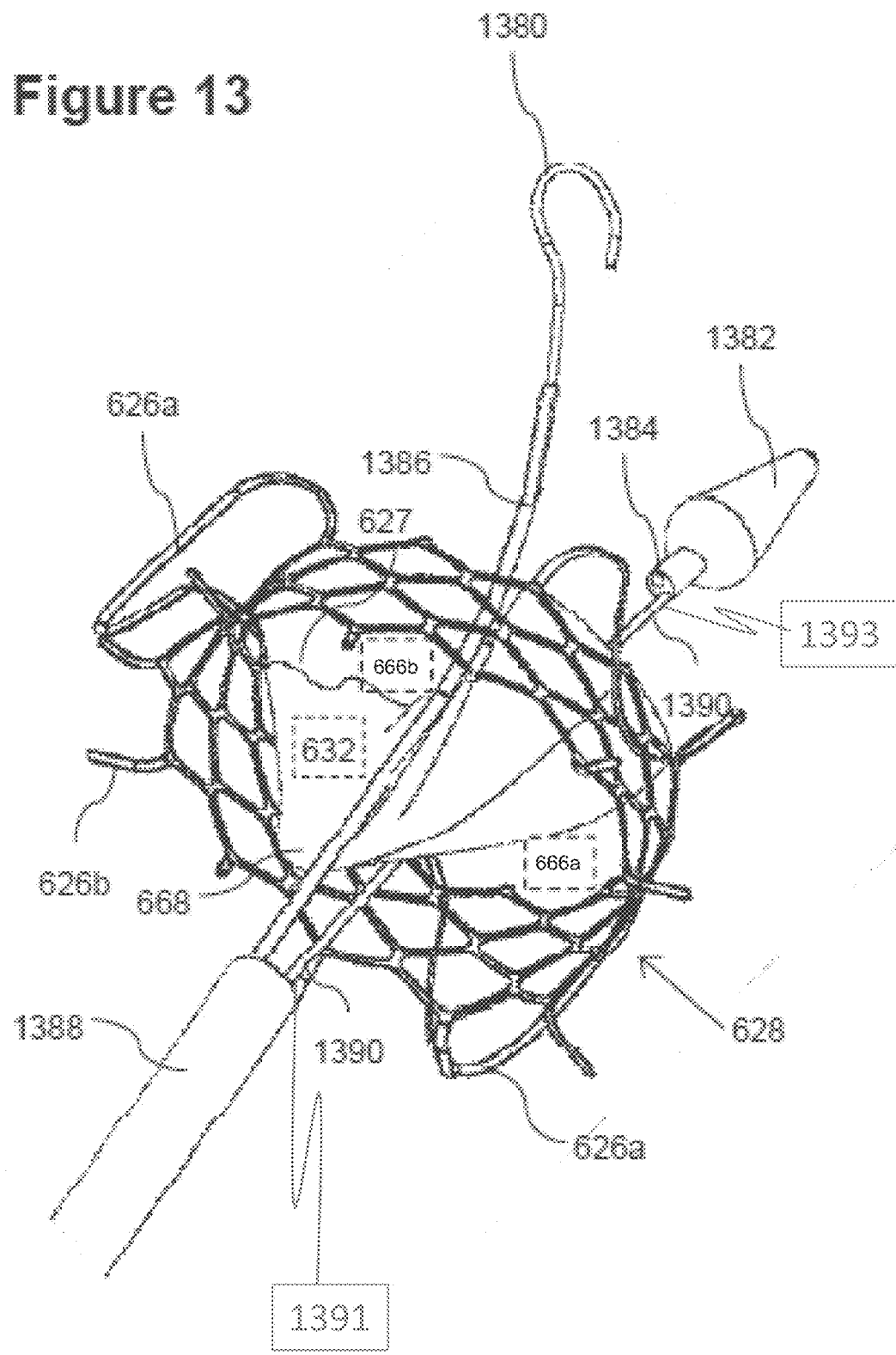
FIG. 13 is a close up perspective illustration of a prosthetic valve and deployment system with the frame expanded and the valve open in accordance with some embodiments.

FIG. 13 is a close up perspective illustration of a prosthetic valve and deployment system with the frame 628 expanded and the valve open in accordance with some embodiments. A guide wire 1380 optionally passes through a tube 1386 which optionally passes through a peripheral channel 666*b* of the prosthesis. A knurl 1382 includes a proximal opening 1384. Knurl 1382 is held by an extender 1390.

Figure 14:
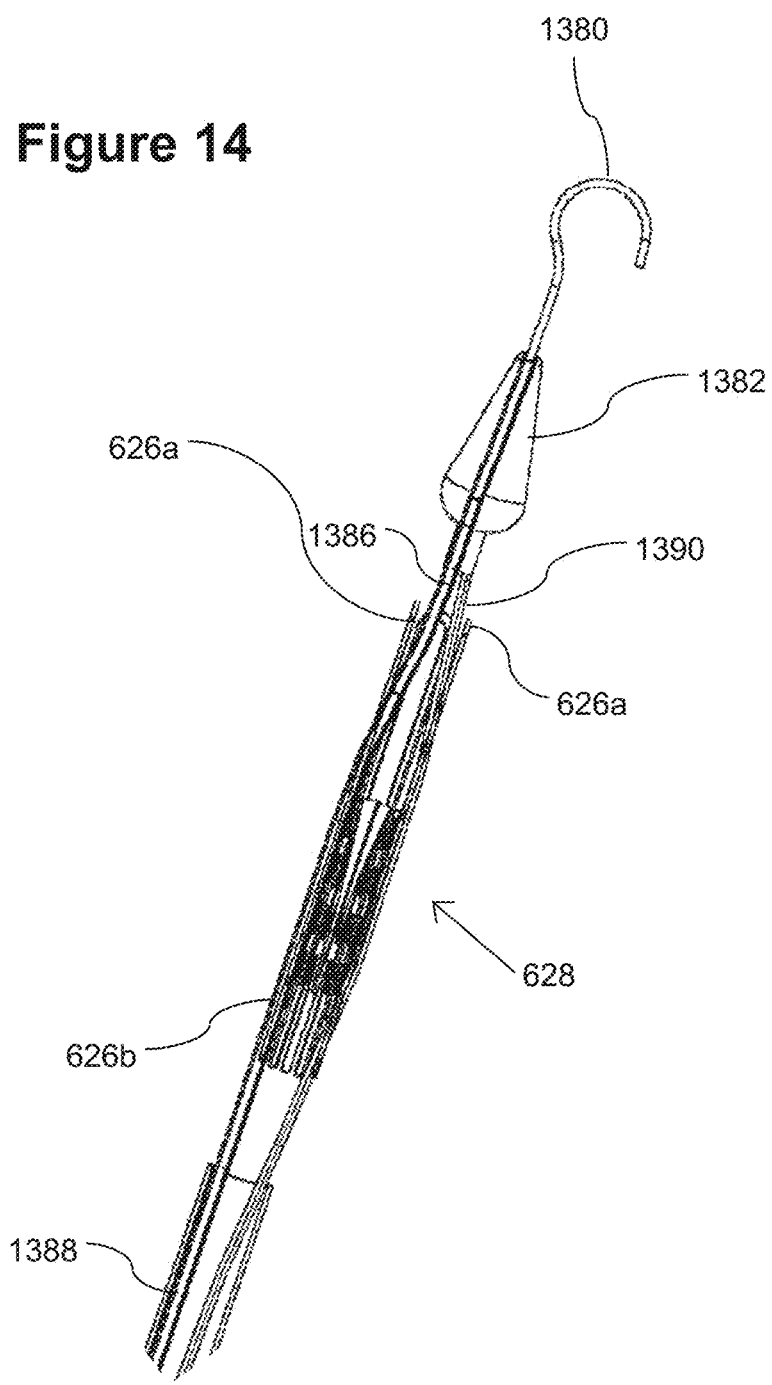
FIG. 14 is a close up perspective illustration of a prosthetic valve and deployment system with the frame collapsed in accordance with some embodiments.

FIG. 14 is a close up perspective illustration of a prosthetic valve and deployment system with the frame 628 collapsed in accordance with some embodiments. Guide wire 1380 has optionally been passed through knurl 1382 locking tube 1386 and/or the prosthesis to a catheter 1388. As long as the guide wire is threaded through the tip, the bioprosthesis is optionally held to catheter 1388. Knurl 1382 is optionally smoothed and/or rounded. The radius of knurl 1382 may range between 0-2 mm and/or from 2 to 5 mm and/or from 5 to 7 mm and/or 7 to 15 mm. The length of knurl 1382 may range between 0 to 4 mm and/or between 5 to 8 mm and/or between 8 to 12 mm and between 12 to 15 mm and/or between 15 to 25 mm.

In some embodiments, while the prosthesis is in its collapsed state guide wire 1380 and delivery knurl 1382, may be used to steer the catheter 1388 for example to arrive through an artery to a treatment zone.

Figure 15:
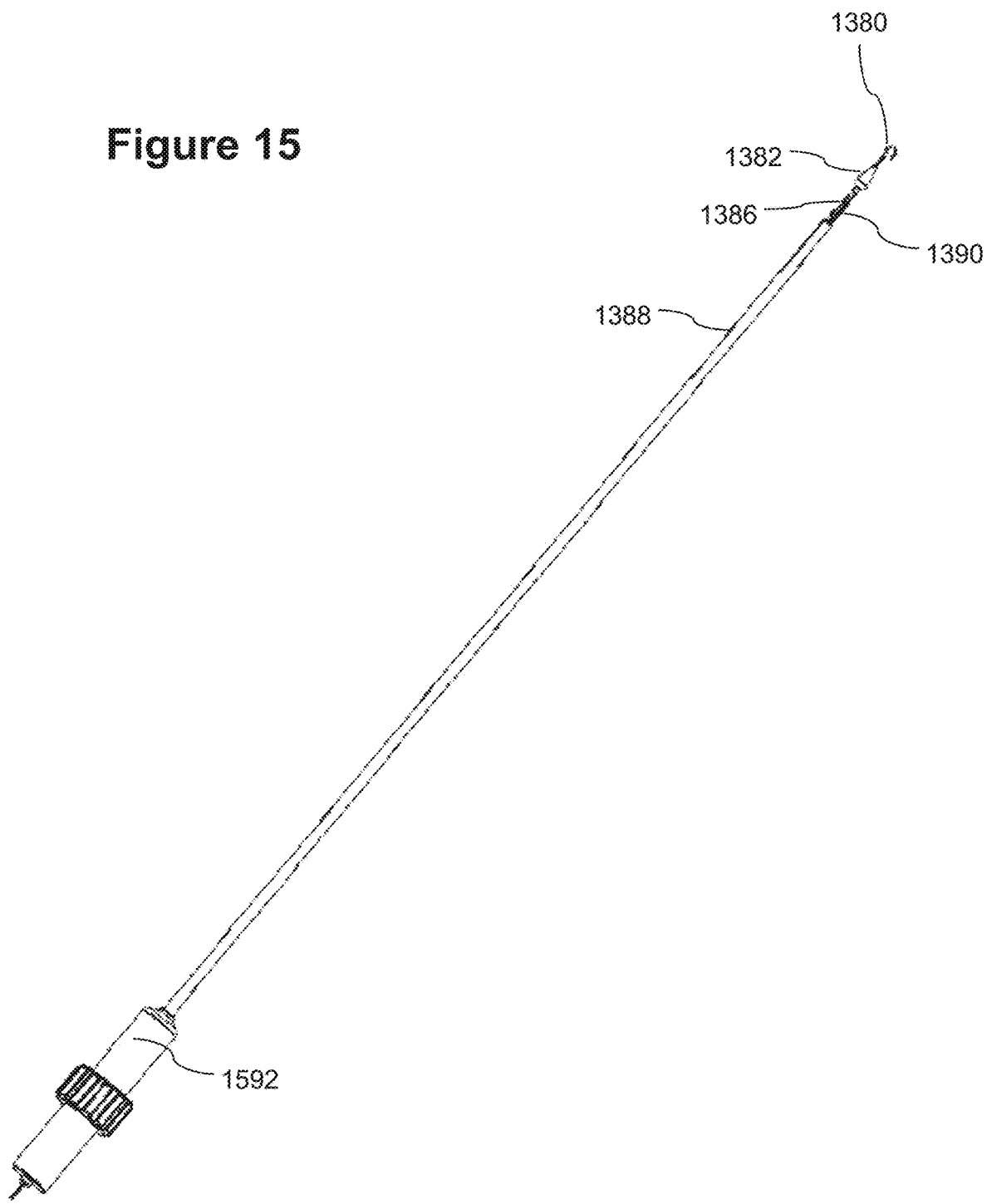
FIG. 15 is a perspective illustration of a prosthetic valve and deployment system with the frame collapsed in accordance with some embodiments.

FIG. 15 is a perspective illustration of a prosthetic valve and deployment system with the frame 628 collapsed in accordance with some embodiments. A catheter controller 1592 is shown. Catheter 1388 diameter may optionally range between 4 to 9 mm (for example 14-28 Fr in the French scale). Delivery system length may optionally range for example between 1 to 25 and/or between 25 to 100 and/or between 100 to 200 cm.

Figure 16:
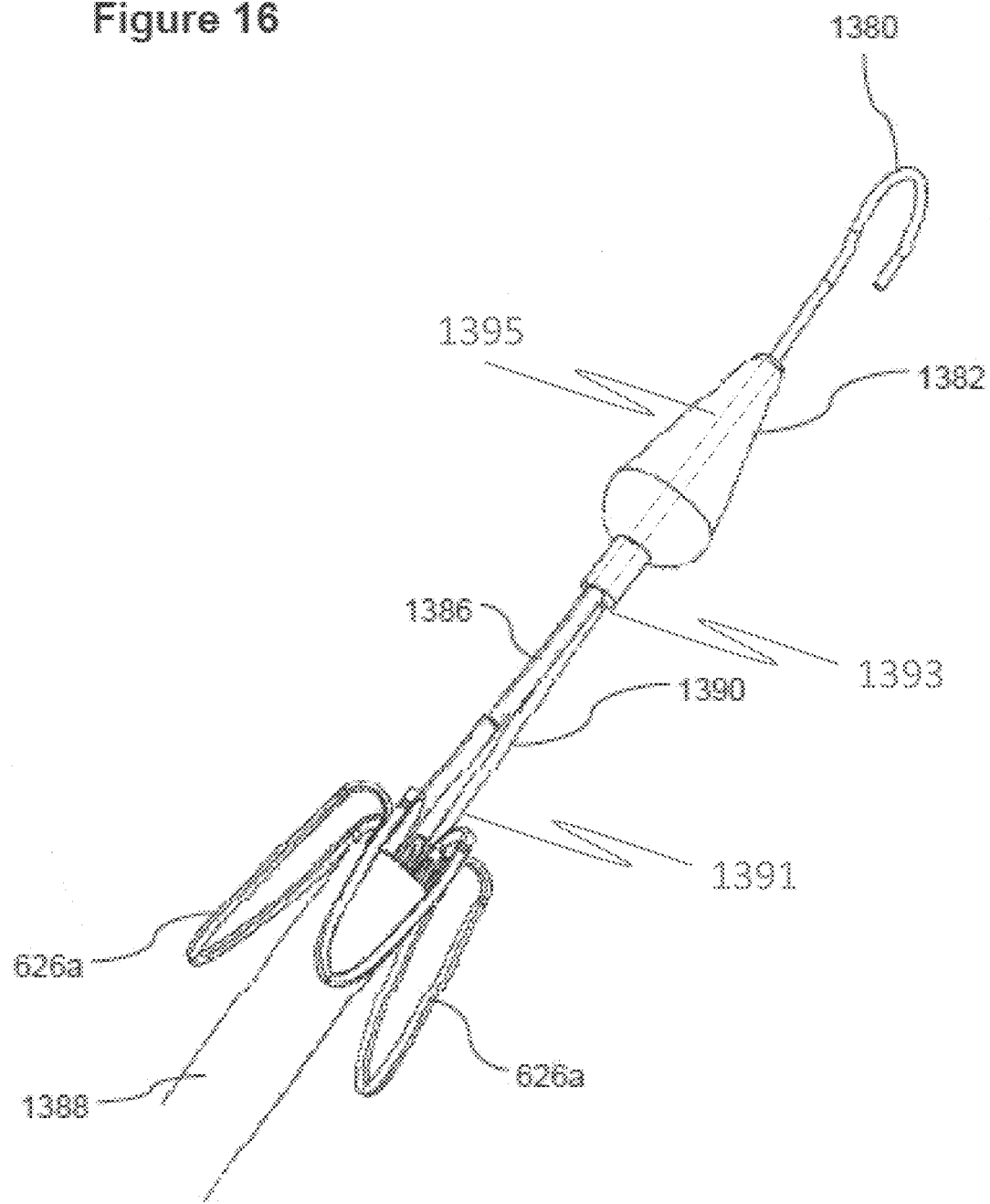
FIG. 16 is a close up perspective illustration of a prosthetic valve and deployment system with the frame collapsed and ventricle stabilizers deployed in accordance with some embodiments.
Figure 17:
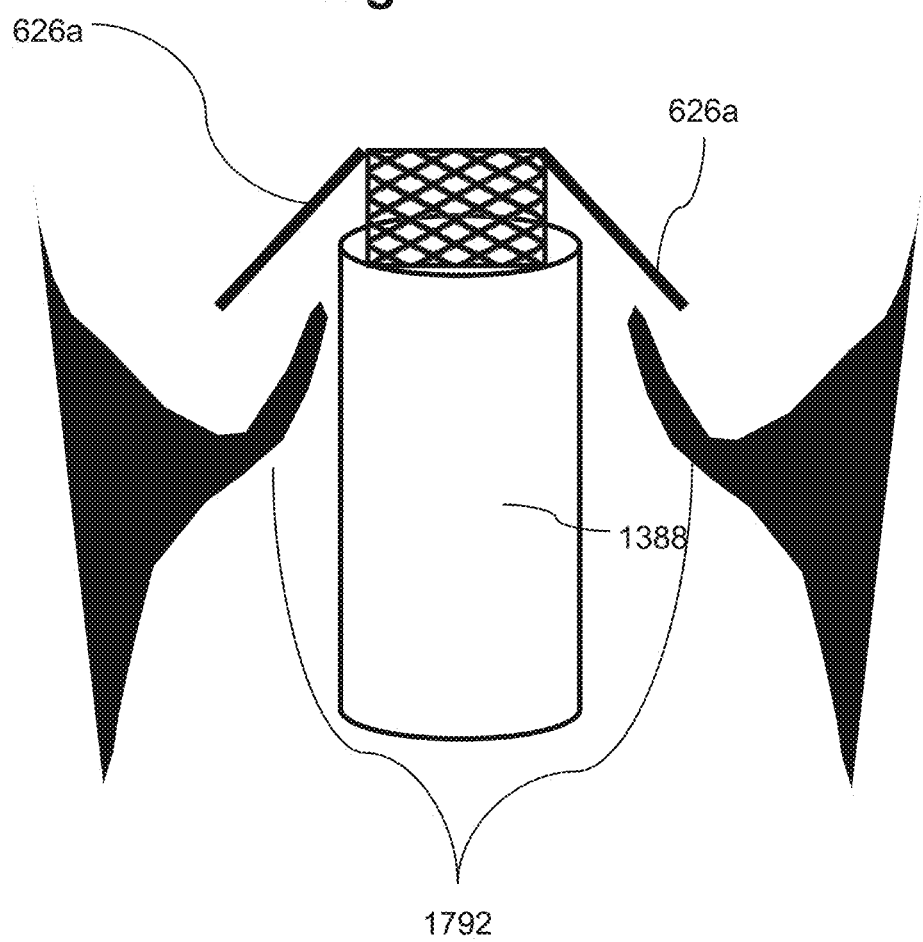
FIG. 17 is a close up perspective illustration of deployment of a prosthetic valve in accordance with some embodiments.

FIG. 16 is a close up perspective illustration of a prosthetic valve and deployment system with the frame 628 collapsed and ventricle stabilizers 626*a* deployed in accordance with some embodiments. For example guide wire 1380 may be inserted through the circulatory system to a right atrium of a patient. Optionally, in the collapsed state (for example as illustrated in FIG. 15) the distal portion of the catheter system may be inserted through the right atrium into the tricuspid annulus into the right ventricle. One the system is in the right ventricle, ventricle stabilizers 626*a* may be deployed (for example as illustrated in FIG. 16). The whole system may optionally be pulled backward (proximally) until ventricle stabilizers 626*a* are in position. For example, ventricle stabilizers 626*a* may be positioned over the native leaflets of the valve (for example leaflets 1792 as illustrated in FIG. 17). Once stabilizers 626*a* are positioned, the delivery catheter 1388 may optionally be pulled away and/or frame 628 may be expanded into the tricuspid annulus. With the valve in place guide wire 1380 may be detached from the knurl 1382 and/or delivery catheter 1388 is optionally pulled back out of the patient for example with the guide wire 1380, tube 1386, extender 1390 and/or delivery knurl 1382 leaving the prosthesis in place.

FIG. 17 is a close up perspective illustration of deployment of a prosthetic valve in accordance with some embodiments. Ventricle stabilizers 626*a* are shown optionally fit over native leaflets 1792.

It is expected that during the life of a patent maturing from this application many relevant technologies (for example delivery methods and/or prosthetic materials) will be developed and the scope of the terms are intended to include all such new technologies a priori. As used herein the term "about" refers to ±5%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Citation or identification of any reference in this application shall not be construed as an admission that such reference is available as prior art to the present invention. To the extent that section headings are used, they should not be construed as necessarily limiting.

What is claimed is:

1. A prosthetic heart valve configured to be anchored between an atrial side of a valve of a heart and a ventricular side of said valve of said heart, comprising:
    a frame sized and shaped to fit in an orifice of a heart valve, said frame having an atrial end configured to be placed at said atrial side and a ventricular end configured to be placed at said ventricular side;
    a flexible diaphragm;
    said frame having a minimum external perimeter and a minimum cross section;
    wherein said frame defines a flow channel;
    wherein an external perimeter of said atrial end of said frame on said atrial end is larger than an external perimeter of said ventricular end of said frame on said ventricular side;
    said flexible diaphragm selectively blocks said flow channel, said flexible diaphragm including an edge at least as large as the minimum external perimeter of the frame and a side of the diaphragm having a surface area greater than the minimum cross section of the frame;
    the flexible diaphragm is connected to the frame at two locations, each location opposite to the other; said connection being along a length ranging between 15% and 50% of a length of the edge using a plurality of suture lines such that a portion of the diaphragm in said each location is held partially expanded along the length by said plurality of suture lines, and said flexible diaphragm acts as a non-still crosspiece across said flow channel and divides said flow channel into at least two channels;
    said plurality of suture lines extending in both a circumferential and an axial direction.

2. The prosthetic heart valve of claim 1, wherein the length of connection of the diaphragm to the frame is along a peripheral portion of the frame.

3. The prosthetic heart valve of claim 1, wherein the flexible diaphragm forms a dome with an apex in an upstream direction.

4. The prosthetic heart valve of claim 1, wherein the frame has a downstream border and wherein the edge of the flexible diaphragm is at least as large as a perimeter of the frame at the downstream border.

5. The prosthetic heart valve of claim 1, wherein the frame surrounds a connected space and the diaphragm divides the connected space into at least two disconnected channels.

6. The prosthetic heart valve of claim 1, wherein the frame has an axial length of between 15 to 25 mm.

7. The prosthetic heart valve of claim 1, wherein the diaphragm has a collapsed position allowing flow from an upstream direction to a downstream direction between the diaphragm and the perimeter of the orifice and an expanded position inhibiting the flow.

8. The prosthetic heart valve of claim 7, wherein the diaphragm includes a free region including an apex of the diaphragm.

9. The prosthetic heart valve of claim 8, wherein in the expanded position, the apex is upstream of the frame.

10. The prosthetic heart valve of claim 1 wherein there is no stiff element connected on two sides to the frame.

11. The prosthetic heart valve of claim 7, wherein said valve is configured to switch from said collapsed position to said expanded position in response to a back flow from a downstream chamber, said back flow occurring between a beginning of a systolic phase until said diaphragm reaches said expanded position and wherein said valve is further configured to permit a back flow volume of between 1 to 40% of a volume of said downstream chamber to flow from said downstream chamber into at least one of a volume of said diaphragm and an upstream chamber.

12. The prosthetic heart valve of claim 1, wherein the diaphragm is connected to the frame along the perimeter of the frame and at a distance less than 20 mm from the edge of said diaphragm.

13. The prosthetic heart valve of claim 1, wherein said flow channel does not include a stiff self-supporting crosspiece.

14. The prosthetic heart valve of claim 1, wherein said flow channel in a portion thereof including the diaphragm does not include a self-supporting crosspiece other than said flexible diaphragm.

15. The prosthetic heart valve of claim 1, wherein said frame comprising one or more ventricular extensions including one or more anchors.

16. The prosthetic heart valve of claim 1, wherein said plurality of suture lines are circumferentially separated from each other.

17. A method of controlling flow through an orifice between an atrial side of a valve of a heart and a ventricular side of said valve of said heart, comprising:
    suspending a diaphragm on a periphery of the orifice; said diaphragm is a flexible diaphragm comprising an edge which is connected to a frame;
    said frame sized and shaped to fit in said orifice of said heart valve, said frame having an atrial end configured to be placed at said atrial side and a ventricular end configured to be placed at said ventricular side; said frame having a minimum external perimeter and a minimum cross section; wherein said frame defines a flow channel; wherein an external perimeter of said atrial end of said frame on said atrial end is larger than an external perimeter of said ventricular end of said frame on said ventricular side;
    said flexible diaphragm selectively blocks said flow channel, and said edge of said flexible diaphragm being at least as large as the minimum external perimeter of the frame and a side of the diaphragm having a surface area greater than the minimum cross section of the frame; said connection of said flexible diaphragm being at two locations, each location opposite to the other; said connection being along a length ranging between 15% and 50% of a length of said edge using a plurality of suture lines such that a portion of said diaphragm in said each location is held partially expanded along said length by said plurality of suture lines, and said flexible diaphragm acts as a non-still crosspiece across said flow channel and divides said flow channel into at least two channels; said plurality of suture lines extending in both a circumferential and an axial direction;
    collapsing the diaphragm by means of a pressure gradient in a first direction through the orifice the pressure gradient in the first direction driving flow passing between the periphery and the diaphragm on at least on two sides of the diaphragm;
    filling the diaphragm with regurgitated fluid driven by a second pressure gradient in a second direction opposite the first direction, and
    pressing the diaphragm against a periphery of the orifice by fluid pressure from the second gradient.

18. The method of controlling of claim 17, further including:
   fitting a frame into orifice and wherein the suspending is from a frame fit into the orifice.

19. The method of controlling of claim 17, further comprising:
   resuming the pressure gradient in the first direction after the filling and
   returning at least 80% of the regurgitated fluid back through the orifice during the resuming.

20. The method of controlling of claim 17, further comprising:
   permitting back flow from a downstream chamber of between 1 to 40% of a volume of said downstream chamber driven into said orifice by said second pressure gradient; and
   closing said orifice to further back flow as a result of said pressing; said closing subsequent to said permitting.

* * * * *